US008691992B2

(12) United States Patent
Loh et al.

(10) Patent No.: US 8,691,992 B2
(45) Date of Patent: Apr. 8, 2014

(54) OCTAHYDRO BIQUINOLINE COMPOUND

(75) Inventors: Teck Peng Loh, Singapore (SG); Jian Xiao, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/262,604

(22) PCT Filed: May 17, 2010

(86) PCT No.: PCT/SG2010/000188
§ 371 (c)(1),
(2), (4) Date: Dec. 28, 2011

(87) PCT Pub. No.: WO2010/132029
PCT Pub. Date: Nov. 18, 2010

(65) Prior Publication Data
US 2012/0088916 A1    Apr. 12, 2012

Related U.S. Application Data

(60) Provisional application No. 61/178,722, filed on May 15, 2009.

(51) Int. Cl.
*C07D 215/38*    (2006.01)
(52) U.S. Cl.
USPC ........................................................ 546/157
(58) Field of Classification Search
USPC ........................................................ 546/157
See application file for complete search history.

(56) References Cited

PUBLICATIONS

Blakemore, J Org Chem, vol. 71, pp. 8212-8218, 2006.*
Akiyama et al., "Enantioselective Mannich-Type Reaction Catalyzed by a Chiral Brønsted Acid," *Angew. Chem. Int. Ed.*43: 1566-1568, 2004.
Akiyama et al., "Recent Progress in Chiral Brønsted Acid Catalysis," *Adv. Synth. Catal.* 348: 999-1010, 2006.
Akiyama, "Stronger Brønsted Acids," *Chem. Rev.* 107: 5744-5758, 2007.
Allenmark, "Chiroptical methods in the stereochemical analysis of natural products," *Nat. Prod. Rep.* 17: 145-155, 2000.
Blakemore et al., "Harnessing Anionic Rearrangements on the Benzenoid Ring of Quinoline for the Synthesis of 6,6'-Disubstituted 7,7'-Dihydroxy-8,8'-biquinolyls," *J. Org. Chem.* 70: 373-376, 2005.
Blakemore et al., "Resolution, Enantiomerization Kinetics, and Chiroptical Properties of 7,7'-Dihydroxy-8,8'-biquinolyl," *J. Org. Chem.* 71: 8212-8218, 2006.
Blakemore et al., "Enzymatic Resolution of 7,7'-Dihydroxy-8,8'-biquinolyl Dipentanoate and Its Conversion to 2,2'-Di-*tert*-butyl-7,7'-dihydroxy-8,8'-biquinolyl," *J. Org. Chem.* 72: 9368-9371, 2007.
Chen et al., "Modified BINOL Ligands in Asymmetric Catalysis," *Chem. Rev.* 103: 3155-3211, 2003.

Connon, "Chiral Phosphoric Acids: Powerful Organocatalysts for Asymmetric Addition Reactions to Imines," *Angew. Chem. Int. Ed.* 45: 3909-3912, 2006.
Ding et al., "A Novel Two-Phase Oxidative Coupling of 2-Naphthols Suspended in Aqueous $Fe^{3+}$ Solutions," *Tetrahedron* 52(3): 1005-1010, 1996.
Doyle and Jacobsen, "Small-Molecule H-Bond Donors in Asymmetric Catalysis," *Chem. Rev.* 107: 5713-5743, 2007.
Fabbri and Delogu, "A Widely Applicable Method of Resolution of Binaphthyls: Preparation of Enantiomerically Pure 1,1'-Binaphthalene-2,2'-diol, 1,1'-Binaphthalene-2,2'-dithiol, 2'-Mercapto-1,1'-binaphthalen-2-ol, and 1,1'-Binaphthalene-8,8'-diol," *J. Org. Chem.* 60: 6599-6601, 1995.
Harper et al., "Stereochemical Analysis by Solid-State NMR: Structural Predictions in Ambuic Acid," *J. Org. Chem.* 68(12): 4609-4614, 2003.
Jiang and Lu, "Synthesis of (±) Binaphthols Via Oxidative Coupling of Naphthols by Cerium Ammonium Nitrate (CAN)," *Synthetic Communications* 31(1): 131-134, 2001.
Noji et al., "A New Catalytic System for Aerobic Oxidative Coupling of 2-Naphthol Derivatives by the Use of CuCl-Amine Complex: A Practical Synthesis of Binaphthol Derivatives," *Tetrahedron Letters* 35(43): 7983-7984, 1994.
Pine et al., *Organic Chemistry 4th edition*, McGraw-Hill Book Company, Singapore, 1981, Chapter 4-2, "Conformations of Acyclic Compounds," pp. 97-99 and 115-119.
Riccio et al., "Stereochemical analysis of natural products. Approaches relying on the combination of NMR spectroscopy and computational methods," *Pure Appl. Chem.* 75(2-3): 295-308, 2003.
Schanz et al., "Improved resolution for (*R,R*)- and (*S,S*)-cyclohexane-1,2-diamine and (*R*)- and (*S*)-BINOL," *Tetrahedron: Asymmetry* 14: 2763-2769, 2003.
Smith and March, *March's Advanced Organic Chemistry: Reactions, Mechanisms, and Structure*, 6th Edition, John Wiley & Sons, Inc., Hoboken, New Jersey, 2007, pp. 155-158.
Terada, "Binaphthol-derived phosphoric acid as a versatile catalyst for enantioselective carbon-carbon bond forming reactions," *Chem. Commun.* 4097-4112, 2008.

(Continued)

*Primary Examiner* — D M Seaman
(74) *Attorney, Agent, or Firm* — Seed IP Law Group PLLC

(57) ABSTRACT

The present invention relates to an octahydro biquinoline compound. Provided is also a method of separating the octahydro biquinoline compound into enantiomers. The octahydro biquinoline compound is of the general formula (V): In formula (V) $R^1$ is one of H, a protective group and an aliphatic group, with the aliphatic group having a main chain of a length of 1 to about 10 carbon atoms, comprising 0 to about 6 heteroatoms selected from the group consisting of N, O, S, Se and Si. $R^2$ and $R^3$ are independent from one another selected from the group consisting of (i) H, (ii) one of an aliphatic, an alicyclic, an aromatic, an arylaliphatic, and an arylalicyclic group comprising 0 to about 6 heteroatoms selected from the group consisting of N, O, S, Se and Si, an ester, a carbonate group, a carbamoyl group and a phosphate ester. $R^4$ and $R^5$ are independent from one another H, an aliphatic, an alicyclic, an aromatic, an arylaliphatic or an arylalicyclic group comprising 0 to about 6 heteroatoms selected from the group consisting of N, O, S, Se and Si.

10 Claims, 13 Drawing Sheets

(56) References Cited

PUBLICATIONS

Uraguchi and Terada, "Chiral Brønsted Acid-Catalyzed Direct Mannich Reactions via Electrophilic Activation," *J. Am. Chem. Soc.* 126: 5356-5357, 2004.

Vyskočil et al., "Copper(II)-Mediated Oxidative Coupling of 2-Aminonaphthalene Homologues. Competition between the Straight Dimerization and the Formation of Carbazoles," *J. Org. Chem.* 66: 1359-1365, 2001.

Wang et al., "Practical Method and Novel Mechanism for Optical Resolution of BINOL by Molecular Complexation with *N*-Benzylcinchoninium Chloride," *Tetrahedron* 56: 4447-4451, 2000.

Xiao and Loh, "Design, Synthesis and Optical Resolution of New Bifunctional Ligand: 1,1'- Dimethyl-octahydro-8,8'-Biquinoline-7,7'-diol," *Organic Letters* 11(13): 2876-2879, 2009.

\* cited by examiner

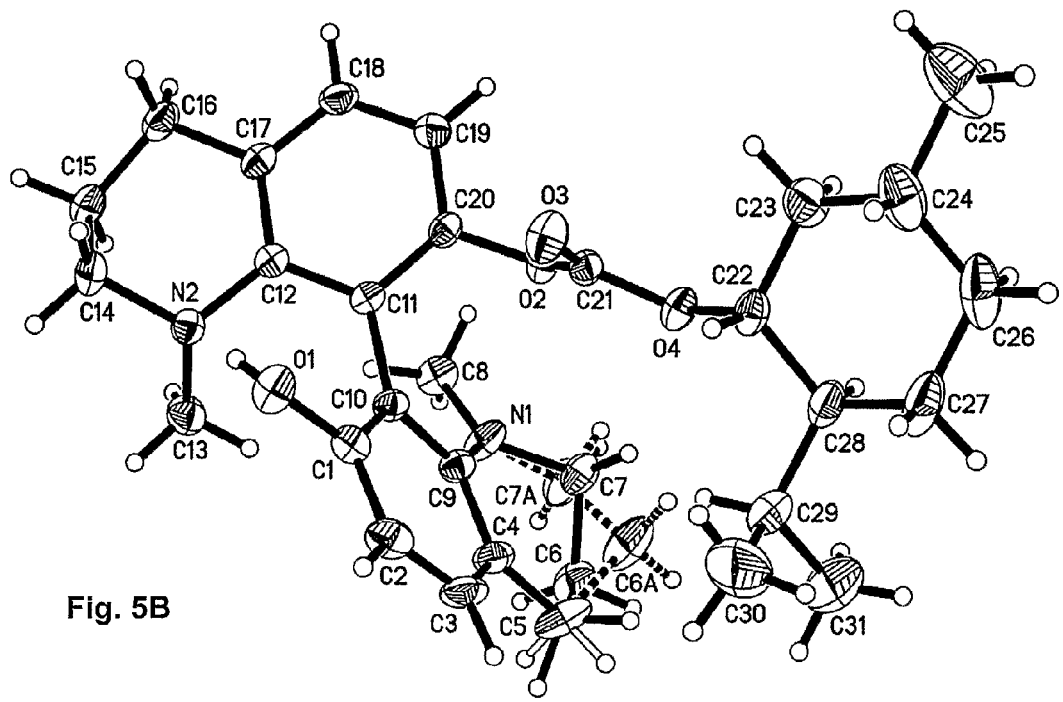
Fig. 5B
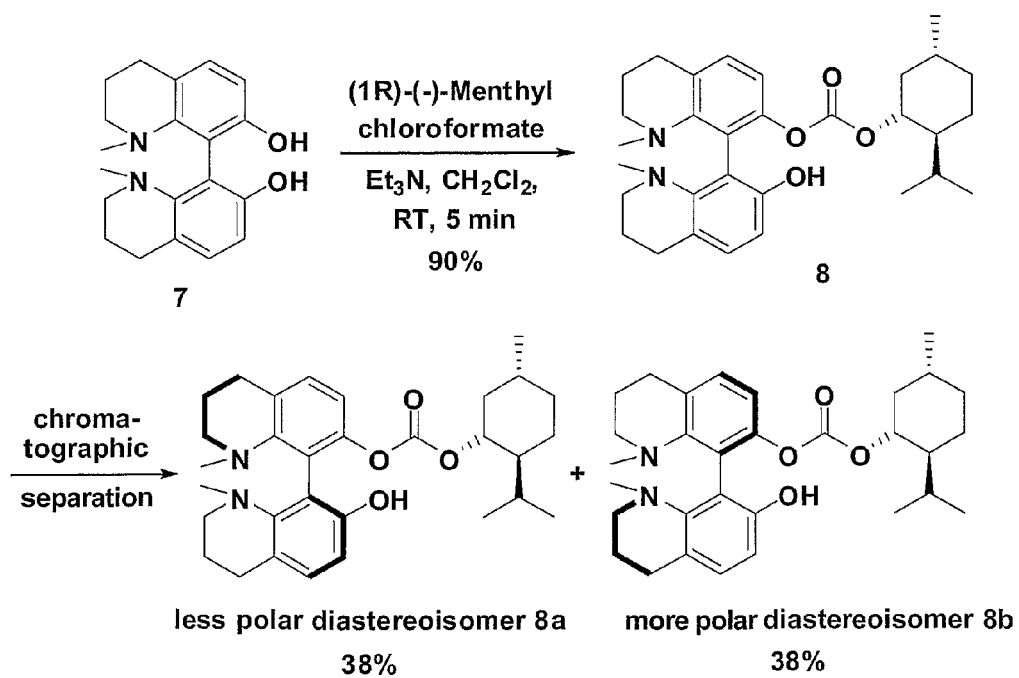
less polar diastereoisomer 8a
38%
more polar diastereoisomer 8b
38%
Fig. 6 (cont. on next page)

(cont. from prev. page)

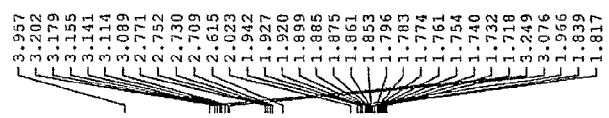
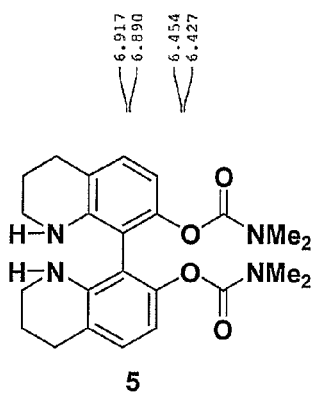
Fig. 10A
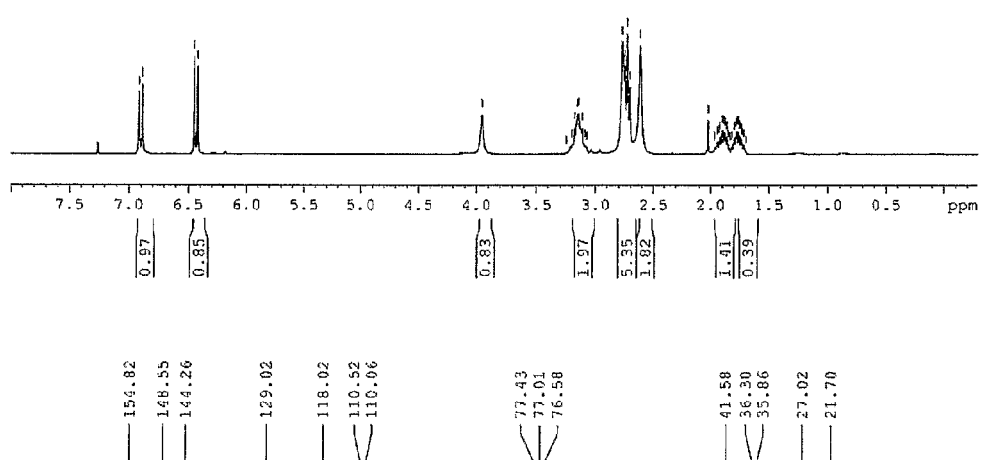
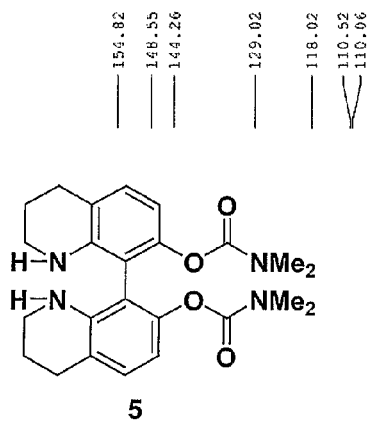
Fig. 10B
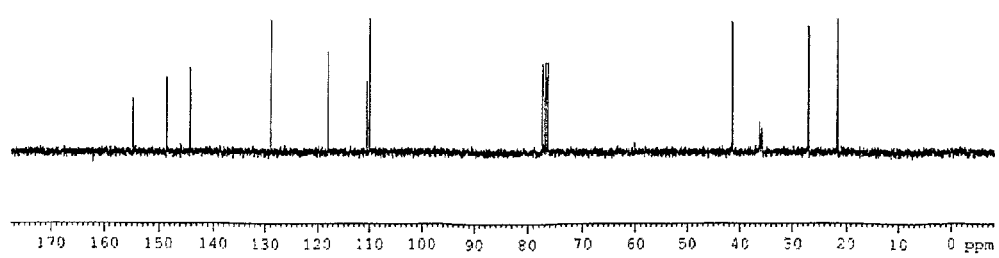

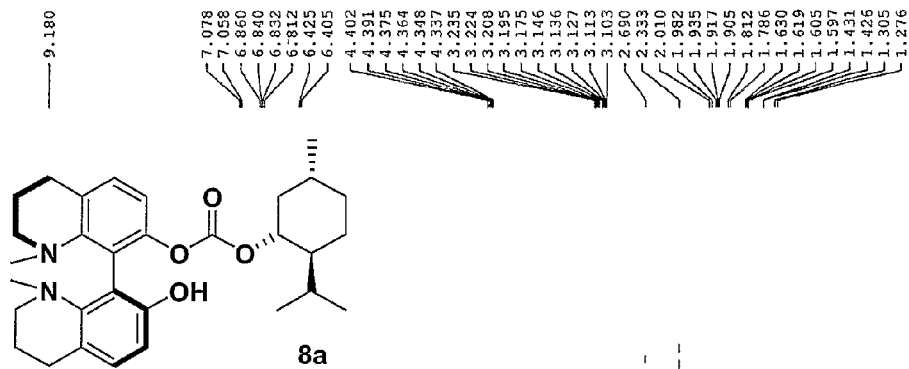
Fig. 13A
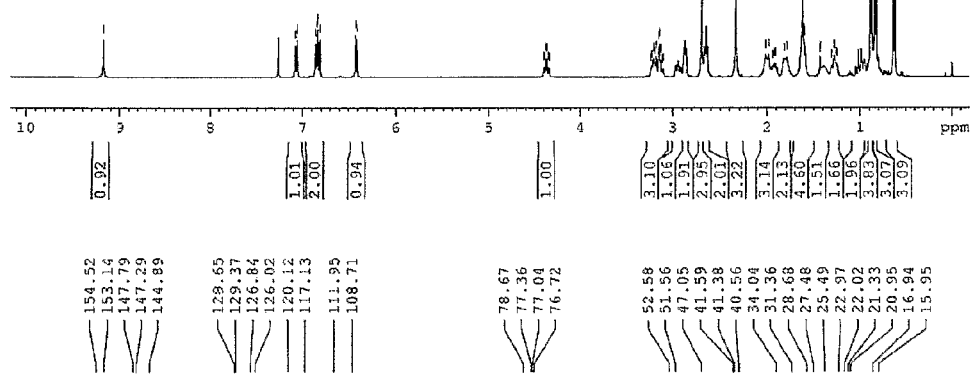
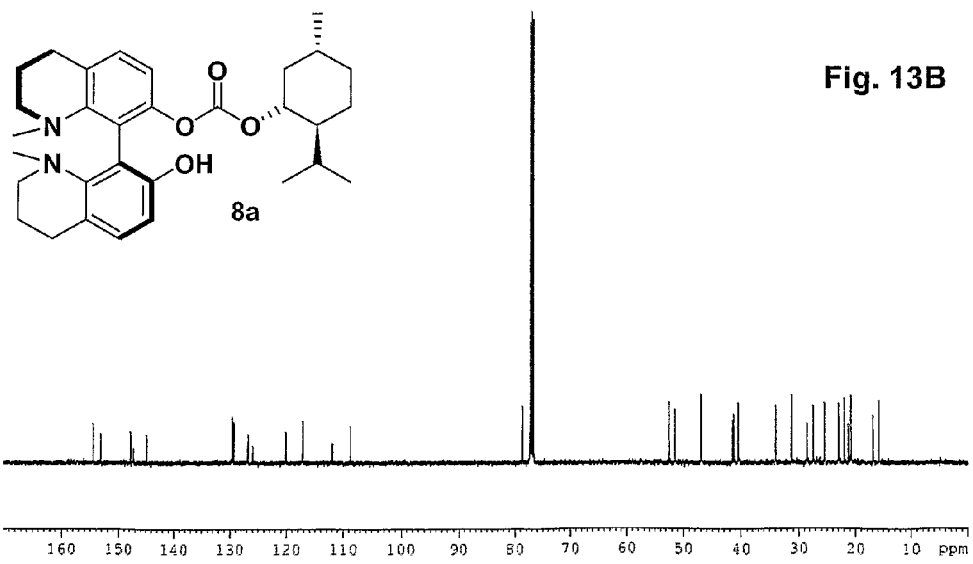
Fig. 13B

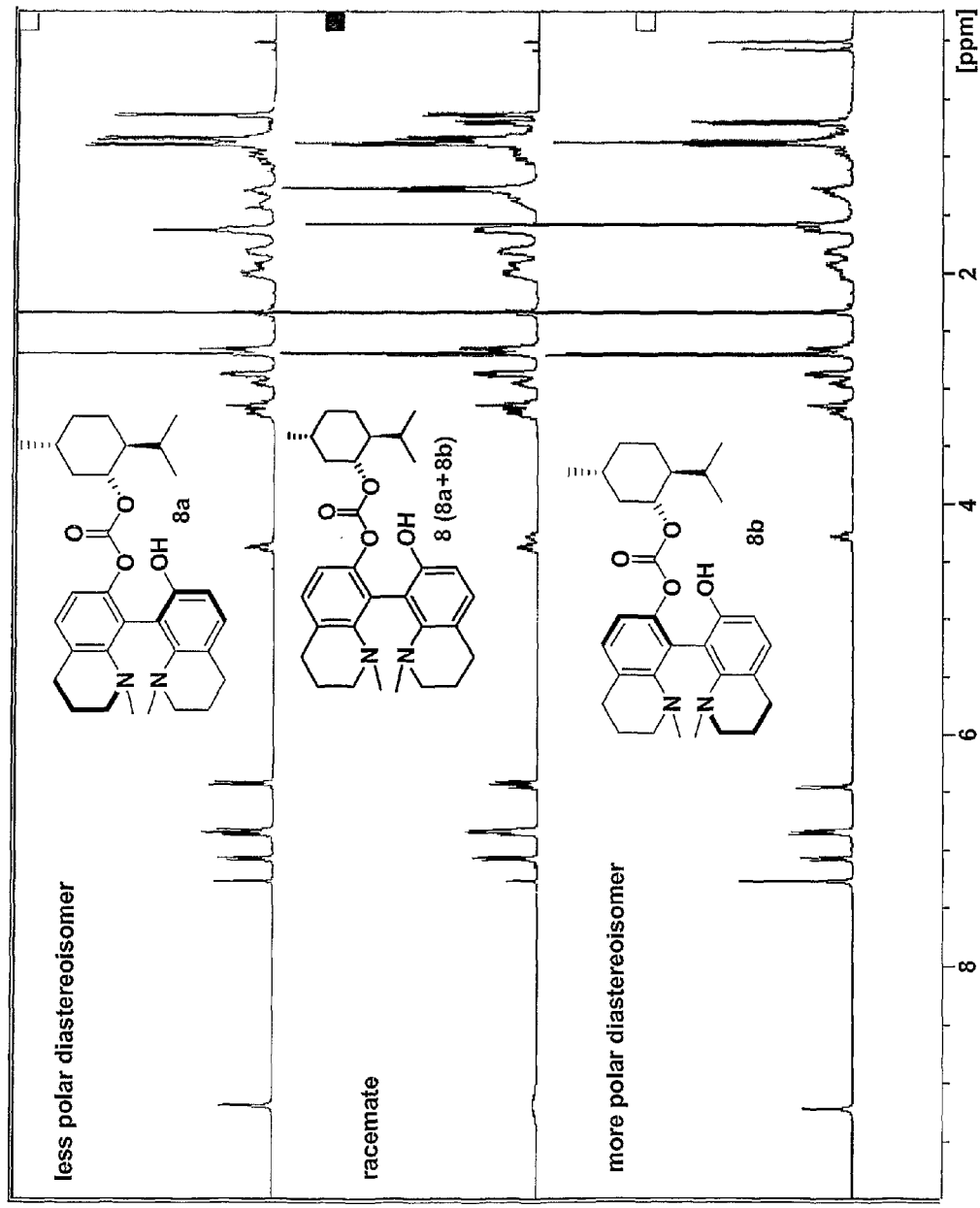

OCTAHYDRO BIQUINOLINE COMPOUND

CROSS REFERENCE TO RELATED APPLICATIONS

This application is a U.S. National Phase Application of International Application No. PCT/SG2010/000188, filed May 17, 2010; which application makes reference to and claims the benefit of priority of a provisional application for the "Design, Synthesis Design, Synthesis and Optical Resolution of New Bifunctional Ligand: 1,1'-Dimethyl-octahydro-8,8'-Biquinoline-7,7'-diol" filed on May 15, 2009 with the United States Patent and Trademark Office, and there duly assigned Ser. No. 61,178,722. The content of said application filed on May 15, 2009 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to an octahydro biquinoline compound. Provided is also a method of separating the octahydro biquinoline compound into enantiomers.

BACKGROUND OF THE INVENTION

Development of new effective chiral auxiliaries, catalysts and ligands continues to be an important endeavour in the field of organic chemistry because novel classes of chiral auxiliaries, catalysts and ligands not only offer additional synthetic opportunities but also provide new insights into fundamental chemical processes and new applications. Enantiomerically pure 1,1'-binaphthyl-2,2'-diol (BINOL) has been extensively utilized as a chiral auxiliary and ligand for both stoichiometric and catalytic asymmetric synthesis due to its axial dissymmetry and molecular flexibility. Of all the widely employed chiral ligands, the axially chiral 1,1'-binaphthyl-2,2'-diol (BINOL) has emerged as one of the most powerful ligands in asymmetric catalysis. The biaryl motif of this compound is considered to be a privileged structure in asymmetric catalysis.

Furthermore, BINOL-based synthons have become attractive molecular modules for applications in many fields such as chiral supramolecular recognition, crystal engineering and electronic materials. In this context a modification of the BINOL backbone would be highly valuable.

Efforts to modify the BINOL backbone lead to derivatives with different substituents at the C-3, C-4, C-6 and C-7 positions (Chen, Y, et al., Chem. Rev. (2003) 103, 3155). Notably, the rotational barrier of peri C—H bonds contributed significantly to the configurational stability of BINOL, hence direct modification of this special moiety provides another important strategy to change its scaffold. In addition, the chiral core defined by the two naphthyl rings provides an ideal chiral environment for the transfer of stereoinformation. The functionalization of the 8,8'-positions was also believed to have interesting implications in asymmetric induction. For example, $F_8$-BINOL, $H_8$-BINOL and $H_4$-BINOL have been used to facilitate some asymmetric reactions with better enantioselectivities than BINOL itself.

It would thus be desirable to have further compounds with a backbone that is similar to that of BINOL, in particular for asymmetric synthesis. It is therefore an object of the present invention to provide a further derivative or analogue with a backbone that is similar to BINOL. This object is solved by the compound of claim 1.

SUMMARY OF THE INVENTION

In a first aspect the invention provides an octahydro biquinoline compound of the general formula (V):

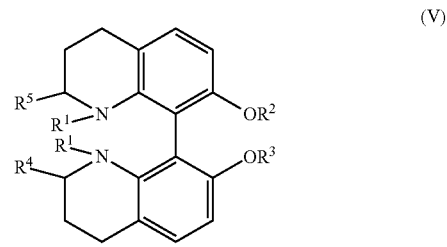

In this formula $R^1$ may be H, a protective group or an aliphatic group that has a main chain of a length of 1 to about 10 carbon atoms. The main chain of such an aliphatic group includes 0-6 heteroatoms (i.e. atoms that differ from carbon). A respective heteroatom may be N, O, S, Se or Si. $R^2$ and $R^3$ in Formula (V) may independent from one another be H. $R^2$ and $R^3$ may independent from one another also bean aliphatic, an alicyclic, an aromatic, an arylaliphatic, and an arylalicyclic group with a main chain of a length of 1 to about 30 carbon atoms. The main chain of such an aliphatic, alicyclic, aromatic, arylaliphatic or arylalicyclic group may include 0 to about 6 heteroatoms (i.e. atoms that differ from carbon). A respective heteroatom may be N, O, S, Se and Si. $R^2$ and $R^3$ may independent from one another also be an ester group [—O]—C(O)—$R^{11}$. Further, $R^2$ and $R^3$ may independent from one another also be a carbonate group [—O]—C(O)—O—$R^{11}$, a carbamoyl group [—O]—C(O)—N($R^{11}$)—$R^{12}$ or a phosphate ester [—O]—P(O)(O$R^{11}$)—O$R^{12}$. Brackets [ ] in these formulas indicate that the oxygen atom is already indicated in formula (V). $R^{11}$ in the ester group, the carbonate group, the carbamoyl group and the phosphate ester, and $R^{12}$ in the carbamoyl group and the phosphate ester are independent from one another H or one of an aliphatic, an alicyclic, an aromatic, an arylaliphatic, and an arylalicyclic group. A respective aliphatic, alicyclic, aromatic, arylaliphatic, and an arylalicyclic group may have a main chain that includes 0 to about 6 heteroatoms selected from N, O, S, Se and Si. In some embodiments the respective main chain includes 1 to about 20 carbon atoms. In some embodiments one of $R^2$ and $R^3$ defines an aliphatic, aromatic or arylaliphatic bridge or a phosphate ester bridge that is linked to the respective other moiety of $R^3$ and $R^2$. Accordingly, $R^2$ and $R^3$ may in some embodiments define one common cyclic structure. $R^4$ and $R^5$ in formula (V) may be H. $R^4$ and $R^5$ may also be independent from one another an aliphatic, an alicyclic, an aromatic, an arylaliphatic or an arylalicyclic group with a main chain of a length of 1 to about 30 carbon atoms. The main chain of such an aliphatic, alicyclic, aromatic, arylaliphatic or aryl alicyclic group may include 0 to about 6 heteroatoms. A respective hetero atom may be N, O, S, Se and Si.

In a second aspect the inventions provides a method of forming an octahydro biquinoline compound according to the first aspect. The method includes providing a biquinolyl compound of general formula (VI)

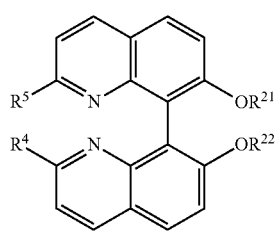

In this formula $R^4$ and $R^5$ are independent from one another H, an aliphatic, an alicyclic, an aromatic, an arylaliphatic or an arylalicyclic group. The main chain of such an aliphatic, alicyclic, aromatic, arylaliphatic or arylalicyclic group may have a main chain of 1 to about 30 carbon atoms. Further, the main chain of such an aliphatic, alicyclic, aromatic, arylaliphatic or arylalicyclic group may include 0 to about 6 heteroatoms. A respective heteroatom may be N, O, S, Se and Si. $R^{21}$ and $R^{22}$ in formula (VI) may be H. $R^{21}$ and $R^{22}$ in formula (VI) may independent from one another also be one of an aliphatic, an alicyclic, an aromatic, an arylaliphatic, and an arylalicyclic group. Such an aliphatic, alicyclic, aromatic, arylaliphatic or arylalicyclic group may have a main chain of about 1 to about 30 carbon atoms. The main chain of a respective aliphatic, alicyclic, aromatic, arylaliphatic or arylalicyclic group may include 0 to about 6 heteroatoms selected from the group consisting of N, O, S, Se and Si. $R^{21}$ and $R^{22}$ in formula (VI) may independent from one another further be an ester group [—O]—C(O)—$R^{11}$, a carbonate group [—O]—C(O)—O—$R^{11}$ or a carbamoyl group [—O]—C(O)—N($R^{11}$)—$R^{12}$. Brackets [ ] in these formulas indicate that the oxygen atom is already indicated in formula (VI). $R^{11}$ in the ester group, the carbonate group and the carbamoyl group, and $R^{12}$ in the carbamoyl group are independent from one another H or one of an aliphatic, an alicyclic, an aromatic, an arylaliphatic, and an arylalicyclic group. A respective aliphatic, alicyclic, aromatic, arylaliphatic or arylalicyclic group may have a main chain that includes 0 to about 6 heteroatoms selected from N, O, S, Se and Si. The respective main chain of such an aliphatic, alicyclic, aromatic, arylaliphatic or arylalicyclic group includes 1 to about 30, such as 1 to about 20 carbon atoms. In some embodiments one of $R^{21}$ and $R^{22}$ defines an aliphatic, aromatic or arylaliphatic bridge that is linked to the respective other moiety of $R^{21}$ and $R^{22}$. Accordingly, $R^2$ and $R^3$ may in some embodiments define one common cyclic structure. The method further includes exposing the biquinolyl compound of general formula (VI) to hydrogenation in the presence of a suitable catalyst. Thereby the method includes allowing the formation of an octahydro biquinoline compound of general formula (XV)

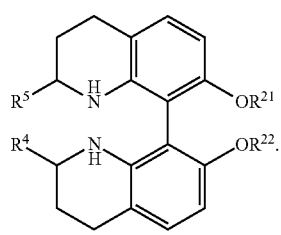

(XV)

In a third aspect the invention provides a method of separating a mixture of enantiomers of the octahydro biquinoline compound according to the first aspect into individual enantiomers of general formula (Va) and general formula (Vb)

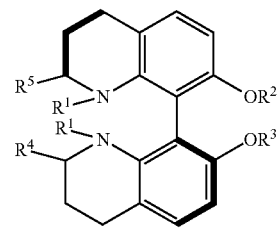

(Va)

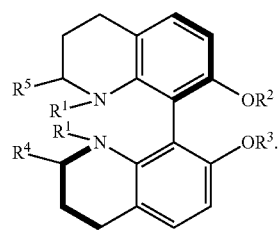

(Vb)

$R^1$ to $R^5$ in formulas (Va) and (Vb) are as defined above. The method includes providing a mixture of enantiomers of the octahydro biquinoline compound of formula (V) (supra). The method further includes contacting the mixture of enantiomers of the octahydro biquinoline compound, i.e. of general formula (Va) and general formula (Vb), with an enantiomer of Menthyl chloroformate. Thereby the method includes allowing the formation of a diastereomeric monomenthyl carbonate of Formula (VIII)

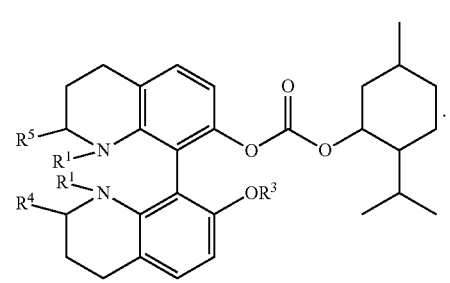

(VIII)

Further, the method includes separating the diastereomers (VIIIa) and (VIIIb)

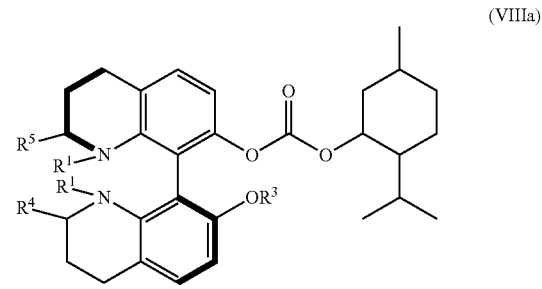

(VIIIa)

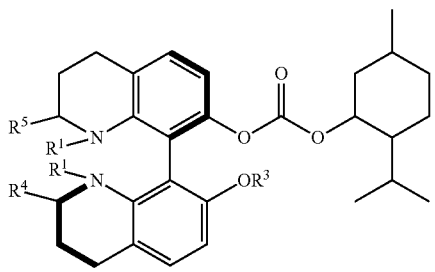

(VIIIb)

In a fourth aspect the invention provides the use of an octahydro biquinoline compound according to the first aspect in asymmetric synthesis.

BRIEF DESCRIPTION OF THE DRAWINGS

The invention will be better understood with reference to the detailed description when considered in conjunction with the non-limiting examples and the accompanying drawings.

FIG. 5B depicts the X-ray crystal structure of compound 8a.

FIG. 10 depicts $^1$H NMR (A) and $^{13}$C NMR (B) spectra of compound 5.

FIG. 13 depicts $^1$H NMR (A) and $^{13}$C NMR (B) spectra of compound 8a.

FIG. 14 depicts $^1$H NMR spectra of 8, 8a and 8b.

DETAILED DESCRIPTION OF THE INVENTION

Figure 1A:
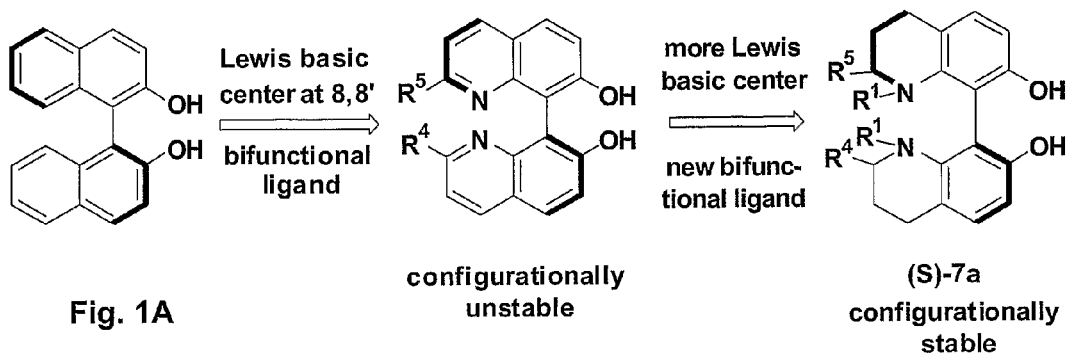
FIG. 1A shows a scheme on the general synthesis strategy to a compound of the invention.

The present invention provides an octahydro biquinoline compound of the general formula (V):

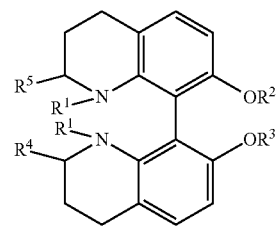

(V)

In this formula $R^1$ may be hydrogen or a protective group. $R^1$ may also be an aliphatic group that has a main chain of a length of 1 to about 12 carbon atoms, such as 1 to about 10 carbon atoms, about 2 to about 10 carbon atoms, 1 to about 8 carbon atoms or about 2 to about 8 carbon atoms, such as 1, 2, 3, 4, 5, 6, 7, 8, 9 or 10 carbon atoms. In addition, the aliphatic group in/of $R^1$, in particular a main chain of the aliphatic group in/of $R^1$ may include 0 to about 6, such as 0 to about 4 or 0 to about 3, e.g., 1, 2, 3, 4, 5 or 6 heteroatoms. Respective heteroatoms may for instance be N, O, S, Se or Si. As a few examples, $R^1$ may be methyl, ethyl, n-propyl, isopropyl, allyl, n-butyl, sec-butyl, isobutyl, tert-butyl, 2-butenyl, 3-butenyl, n-pentyl, isopentyl, neopentyl, 3-methyl-butyl, 2-pentenyl, 3-pentenyl, 3-methyl-2-butenyl or tert-pentyl.

A further example of a respective protective group is a carbamate. Examples of a carbamate include, but are not limited to, methyl carbamate, ethyl carbamate, t-butyl carbamate, allyl carbamate, isopropyl allyl carbamate, 2-chloro ethyl carbamate, 2,2,2-trichloroethyl carbamate, 2-trimethylsilylethyl carbamate, benzyl carbamate, p-methoxybenzyl carbamate, 3,5-di-t-butylbenzyl carbamate, 2-phenylethyl carbamate, 1,1-dimethyl-2,2-dibromo ethyl carbamate, 1,1-dimethyl-2,2,2-trichloro ethyl carbamate, 9-fluorenylmethyl carbamate, 9-(2-sulfo)fluorenylmethyl carbamate, 2-chloro-3-in-denylmethyl carbamate, benz[f]inden-3-ylmethyl carbamate, 2-(2'-pyridyl)ethyl carbamate, 2-[(2-nitrophenyl)dithio]-1-phenylethyl carbamate, cinnamyl carbamate, hexadienyloxy carbamate, propargyloxy carbamate, but-2-ynylbisoxycarbamate, 8-quinolyl carbamate, N-hydroxypiperidinyl carbamate, 4-methylsulfinylbenzyl carbamate, 4-trifluorobenzyl carbamate, carbamate, an alkyldithio carbamate, p-(dihydroxyboryl)-benzyl carbamate, 2-methylthio ethyl carbamate, 2-methylsulfonylethyl carbamate, 2-(4-nitrophenylsulfonyl)ethoxy carbamate, 2-(4-trifluoromethylphenylsulfonyl)ethoxy carbamate, 2-Dansylethyl carbamate, [2-(1,3-dithianyl)]methyl carbamate, 2-(4-nitrophenyl)ethyl carbamate, m-nitrophenyl carbamate and o-nitrobenzyl carbamate.

$R^2$ and $R^3$ are in some embodiments different from each other. In some embodiments $R^2$ and $R^3$ are identical. In formula (V) $R^2$ and/or $R^3$ are in some embodiments a proton, i.e. hydrogen. In some embodiment $R^2$ and $R^3$ are independent from one another one of an aliphatic, alicyclic, aromatic, arylaliphatic, and an arylalicyclic group. The aliphatic, alicyclic, aromatic, arylaliphatic, and arylalicyclic groups of $R^2$ and $R^3$ may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms.

A respective aliphatic, alicyclic, aromatic, arylaliphatic, and arylalicyclic group may include 0 to about 6, such as 0 to about 4, including 1, 2, 3, 4, 5 or 6 heteroatoms. In some embodiments the main chain of the aliphatic, alicyclic, aromatic, arylaliphatic, and an arylalicyclic group includes 0 to about 6, e.g. 1, 2, 3, 4, 5 or 6 heteroatoms. Such a heteroatom may be selected from N, O, S, Se and Si. In some embodiments one or both of $R^2$ and $R^3$ are a protective group. Examples of a suitable protective group include, but are not limited to, an ether, a silyl ether, an ester, a carbonate, an aryl carbamate, a phosphinate and a sulfonate. Illustrative examples of a suitable ether are a methyl-, a t-butyl-, an isopropyl-, a methoxymethyl-, a benzyl-, a 2,4-dimethylbenzyl-, a 4-methoxybenzyl-, an o-nitrobenzyl-, a p-nitrobenzyl-, a 2,6-dichlorobenzyl-, a 3,4-dichlorobenzyl-, a 4-(dimethylamino)carbonylbenzyl-, a methylsulfinylbenzyl-, a benzyloxymethyl-, a methoxyethoxymethyl-, a (2-trimethylsilyl)-ethoxymethyl-, a methylthiomethyl-, a phenylthiomethyl-, an azidomethyl-, a cyano-methyl-, a 2,2-dichloro-1,1-difluoroethyl-, a 2-chloroethyl-, a 2-bromoethyl-, a t-butyldiphenylsilylethyl-, a tetrahydropyranyl-, a 1-ethoxyethyl-, a phenacyl-, a 4-bromo-phenacyl-, a chloropropylmethyl-, an allyl-, a prenyl-, a cyclohexyl-, a cyclohex-2-en-1-yl-, a propargyl-, an anthrylmethyl-, a 4-picolyl-, a heptafluoro-p-tolyl- and a tetrafluoro-4-pyridyl ether. Illustrative examples of a suitable silyl ether are a trimethylsilyl-, a t-butyldimethylsilyl-, a t-butyldiphenylsilyl- and a triisopropylsilyl ether. Illustrative examples of a suitable ester are a formate-, an acetate-, a levulinate-, a pivaloate-, a benzoate-, a 9-fluorenecarboxylate- and a xanthenecarboxylate group. Illustrative examples of a suitable carbonate are a methyl, a t-butyl-, a vinyl-, a benzyl-, an 1-adamantyl-, a 2,4-dimethylpent-3-yl-, an allyl-, a 4-methylsulfinylbenzyl- and a 2,2,2-trichloroethyl carbonate. Illustrative examples of a suitable phosphinate are a dimethylphosphinyl-, a dimethylphosphinothioyl- and a diphenylphosphinothioyl group. Illustrative examples of a suitable sulfonate are a methanesulfonate-, a trifluoromethanesulfonate-, a 2-formylbenzenesulfonate, a toluenesulfonate- and a benzylsulfonate group.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain hetero atoms as for instance N, O, S, Se or Si or carbon atoms may be replaced by these hetero atoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

The term "aromatic" means, unless otherwise stated, an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moietie may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphtho-furanyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxe-pinyl-, azepinyl-, thiepinyl-, selenepinyl-, thioninyl-, azecinyl-, (azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

Accordingly, in some embodiments $R^2$ and/or $R^3$ (as well as $R^4$ and/or $R^5$, see below) in formula (V) is/are an aromatic moiety, such as benzole, imidazole, benzimidazole, 4H-pyran, pyrazole, pyrazine, pyridazine, furan, thiophen, benzofuran, pyridine, bipyridine, indole, 2H-isoindole, naphtalene, anthracene, 9,10-anthracenedione, quinoline, isoquinoline, quinazoline, cinnoline, quinoxaline, thiazine, thiazole, isothiazole, 1H-azepine, dibenzopyridine, azocine, 1H-azonine, oxepine, thiepine, thiaphanthrene (naphtho[2,3-b]thiophene), phenanthro[3,2-b]thiophene, 1-oxa-1H-benz[f]indene (naphtho[2,3-b]furan) and furo[3,2-b]pyridine.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethyl-phenyl)ethyl]-4-ethyl-quinazoline or, 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitroben-zenesulfonyl, and methanesulfonyl.

A heteroatom is any atom that differs from carbon. Examples include, but are not limited to N, O, P, S, and Se. Were several heteroatoms are present within the one or more rings of the aromatic moiety, they are independently selected.

In some embodiment $R^2$ and $R^3$ are one of an ester group [—O]—C(O)—$R^{11}$, a carbonate group [—O]—C(O)—O—$R^{11}$, a carbamoyl group [—O]—C(O)—N($R^{11}$)—$R^{12}$ and a phosphate ester [—O]—P(O)(O$R^{11}$)—O$R^{12}$. In these groups $R^{11}$ and $R^{12}$ are independent from one another H or one of an aliphatic, an alicyclic, an aromatic, an arylaliphatic, and an arylalicyclic group. The aliphatic, alicyclic, aromatic, arylaliphatic, and arylalicyclic groups of $R^{11}$ and $R^{12}$ may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The main chains of a respective aliphatic, alicyclic, aromatic, arylaliphatic or arylalicyclic moiety of $R^1$, $R^2$ or $R^3$ may have 0 to about 5 heteroatoms, such as 0 to about 4 or 0 to about 3, e.g. 0, 1, 2, 3, 4 or 5 heteroatoms. A respective heteroatom may be independently selected one of N, O, S, Se and Si.

Brackets [ ] in the above formulas indicate that the oxygen atom is already indicated in formula (V). The full functional group has merely been indicated for sake of clarity. Accordingly, the ester group may in the context of e.g. formula (V) (as well as e.g. formulas VI, VIII, XV and XVI) also be represented as —C(O)—$R^{11}$, the carbonate group as —C(O)—O—$R^{11}$, the carbamoyl group as —C(O)—N($R^{11}$)—$R^{12}$ and the phosphate ester as —P(O)(O$R^{11}$)—O$R^{12}$.

$R^4$ and $R^5$ may be H. $R^4$ and $R^5$ may also be independent from one another an aliphatic, an alicyclic, an aromatic, an arylaliphatic or an arylalicyclic group. The main chain of such an aliphatic, alicyclic, aromatic, arylaliphatic or arylalicyclic group may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The main chains of a respective aliphatic, alicyclic, aromatic, arylaliphatic or arylalicyclic moiety of $R^1$, $R^2$ or $R^3$ may include 0 to about 6 heteroatoms. A respective heteroatom may be N, O, S, Se and Si. $R^4$ and $R^5$ are in some embodiments different from each other. In some embodiments $R^4$ and $R^5$ are identical. In some embodiments $R^4$ and $R^5$ are coupled to each other, thereby defining a common cyclic structure bridging the two tetrahydroquinolin moieties. In such embodiments one of $R^4$ and $R^5$ may be taken to define an aliphatic, aromatic or arylaliphatic bridge that is linked to the respective other moiety of $R^5$ and $R^4$.

For the compound BINOL, the positions 8 and 8' are thought to be important in terms of configurational stability. Direct modification of this special moiety would thus provide an important strategy to change its scaffold. In addition, the chiral core defined by the two naphthyl rings provides an ideal chiral environment for the transfer of stereoinformation. The exclusive direct functionalization of the 8,8'-positions is also believed to have interesting implications in asymmetric induction. Without being bound by theory the chiral core defined by the 8,8'-positions of BINOL can be illustrated as

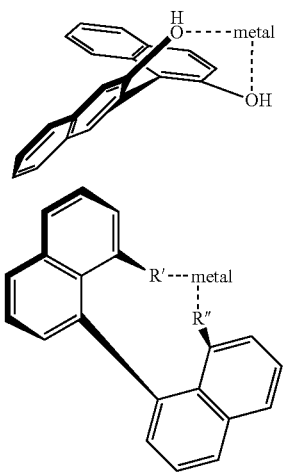

R' and R" in the structure on the right represent a potential functional group at the 8 and the 8' position of BINOL. In contrast thereto, biquinolyl compounds, carrying an N atom at the 8 and the 8' position, have unfortunately been found to be generally configurationally unstable (see FIG. 1B, FIG. 1C). The present inventors have surprisingly found that an octahydro biquinoline compound of formula (V) is, however, configurationally stable. Accordingly, the octahydro biquinoline compound of formula (V) of the invention can be provided in different configurations.

In some embodiments the octahydro biquinoline compound of the general formula (V) is provided in a configuration, which can be represented by formula (Va):

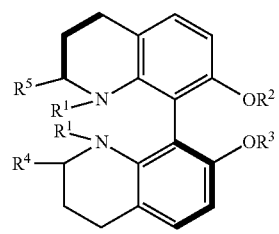

In this formula $R^1$, $R^2$, $R^3$, $R^4$, and $R^5$ are as defined above. In embodiments where both $R^4$ and $R^5$ are hydrogen, this configuration of the octahydro biquinoline compound of the general formula (V) can be represented as

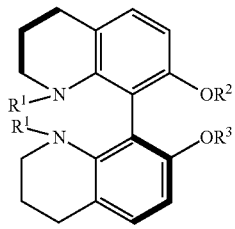

In some embodiments the octahydro biquinoline compound of the general formula (V) is provided in a configuration, which can be represented by formula (Vb):

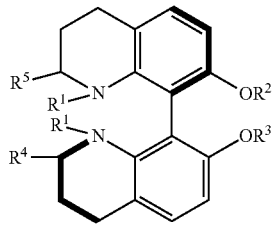

Again, in this formula $R^1$, $R^2$, $R^3$, $R^4$, and $R^5$ are as defined above. In embodiments where both $R^4$ and $R^5$ are hydrogen, this configuration of the octahydro biquinoline compound of the general formula (V) can be represented as

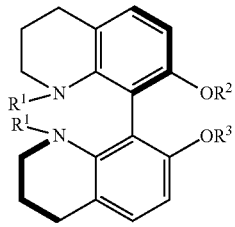

In some embodiments the octahydro biquinoline compound is a mixture of the two enantiomers of Formulas (Va) and (Vb).

In the above structure representations a graphical indication is used to define the stereochemical configuration of the bicyclic moieties. For compound (V) two perpendicular planes can be drawn, neither of which can be bisected by a plane of symmetry. Therefore, two enantiomers (Va) and (Vb) can be distinguished. The indication of the stereo chemical configuration used above is based on the wedge representation, which defines one orientation of a substituent relative to another substituent and relative to a ring structure (see e.g. Pine, Hendrickson, Cram, Hammond: Organic Chemistry, McGraw-Hill, 4th edition, 1981, pages 97-99 & 115-119). By defining nonsuperimposable mirror images the absolute stereochemistry can accordingly be derived. The Cahn-Ingold-Prelog system (R,S system) of nomenclature can, in contrast thereteo, not appropriately be applied on a general basis to compounds of general formula (V) since this system is based on the ranking of substituents, e.g. H<C<N<O or $CH_3$—<$C_2H_5$—<$CH_2$=CH— (see also e.g. Smith, M. B., March, J., Sixth Edition, 2007, Wiley-Interscience, pages 155-158). A compound with the same graphical indication as above (or a wedge representation) is thus in some embodiments called (R) and in other embodiments (S), depending on the nature of the relevant substituents(s). As an example, according to the Cahn-Ingold-Prelog system of nomenclature a compound may in some embodiments termed the (S,S)- and in some embodiments the (R,R)-diastereomer, depending on the selected substituents of a specific embodiment. An indication on the configuration by this system has thus been omitted from formulas (Va) and (Vb) for sake of clarity.

An established standard step in the synthesis of BINOL is an oxidative coupling. This step has, however, by the present inventors been found unsuited for the synthesis of an octahydro biquinoline compound of formula (V) (see the example of FIG. 3). According to the present invention the octahydro biquinoline compound of the general formula (V) can be formed in a process that uses a biquinolyl compound of general formula (VI):

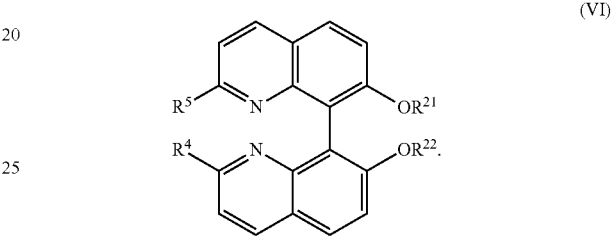

(VI)

In this formula $R^4$ and $R^5$ are as defined above. $R^{21}$ and $R^{22}$ in formula (VI) are selected independently from each other. In some embodiments $R^{21}$ and/or $R^{22}$ are a proton. In some embodiment $R^{21}$ and $R^{22}$ are independent from one another one of an aliphatic, alicyclic, aromatic, arylaliphatic, and an arylalicyclic group. The aliphatic, alicyclic, aromatic, arylaliphatic, and arylalicyclic groups of $R^2$ and $R^3$ may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. In embodiments where both $R^4$ and $R^5$ are hydrogen, biquinolyl compound of general formula (VI) that may be used can be represented as

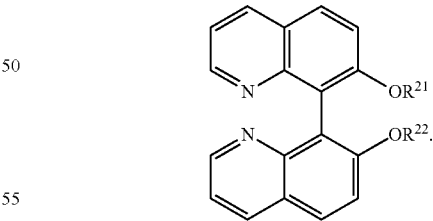

A respective aliphatic, alicyclic, aromatic, arylaliphatic, and arylalicyclic group may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The aliphatic, alicyclic, aromatic, arylaliphatic, and arylalicyclic groups of $R^{11}$ and $R^{12}$ may have a main chain that includes 0 to about 6 heteroatoms, such as 0 to about 4 or 0 to about 3, e.g. 0, 1, 2, 3, 4, 5 or 6 heteroatoms. A respective heteroatom may be independently selected one of N, O, S, Se and Si. In some embodiments one or both of $R^{21}$ and $R^{22}$ are a protective group (supra). In some embodiments $R^{21}$ and $R^{22}$ are identical to the moieties $R^2$ and $R^3$ of formula (V) (cf. above). In such an embodiment the biquinolyl compound can be represented by the formula

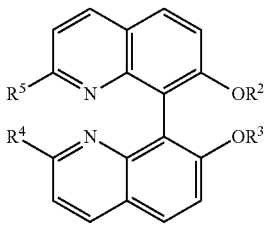

and in embodiments where both $R^4$ and $R^5$ are hydrogen by the formula

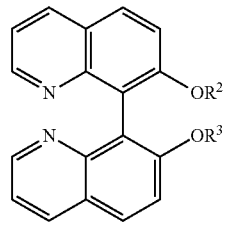

A biquinolyl compound of formula (VI) (supra), in which $R^{21}$ and $R^{22}$ are H can be formed as described by Blakemore et al. (J. Org. Chem. (2006) 71, 21, 8212-8218). As disclosed in the same publication, enantiomerization of a respective biquinolyl compound occurs, which renders any separation of configurations of such a compound meaningless. The present inventors have identified an octahydro biquinoline compound of the general formula (V) (supra) as a suitable alternative.

The moieties $R^4$ and $R^5$ may be introduced as described by Blakemore (2007, supra). An organolithium reagent Li—$R^4$ and/or Li—$R^5$ is/are reacted with a diester of a biquinolyl-dioxy compound or a corresponding carbamate thereof. The respective synthesis is particularly useful in embodiments where $R^4$ and $R^5$ are identical, in which case only one organolithium reagent needs to be used and no separation of different product needs to be carried out. A respective ester may for example be of the formula

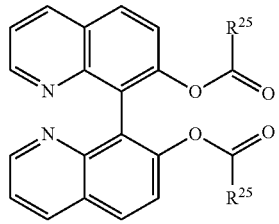

In this formula $R^{25}$ may be an aliphatic, alicyclic, aromatic, arylaliphatic, and arylalicyclic group. A reaction with an organolithium reagent Li—$R^4$ yields for example the following reaction product.

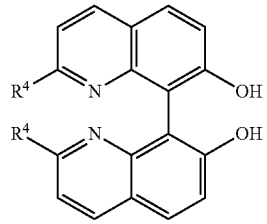

The hydroxyl groups may then be further converted to any desired derivative such as an ether or ester using standard techniques available in the art.

A respective carbamate may for example be of the formula

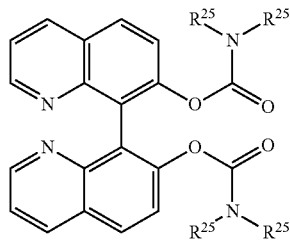

As defined above, $R^{25}$ may be an aliphatic, alicyclic, aromatic, arylaliphatic, and arylalicyclic group. A reaction with an organolithium reagent Li—$R^4$ yields for example the following reaction product.

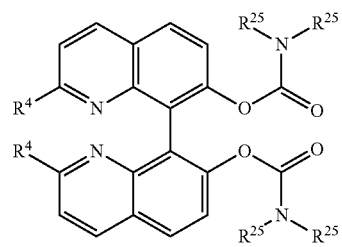

in which the hydroxyl groups of the obtained the biquinolyl compound are already protected, which may be useful if protection is desired.

According to the present invention, a biquinolyl compound of formula (VI) can be converted to a corresponding octahydro biquinoline compound by means of hydrogenation using one of hydrazine, dihydronaphthalene, dihydroanthracene, isopropanol, formic acid or a salt thereof. An illustrative salt of a suitable salt of formic acid is ammonium formate. The hydrogenation is carried out in the presence of a suitable catalyst, such as a metal of group 10 of the periodic table of the elements. Three illustrative examples of a suitable catalyst are Lindlar's catalyst, Pt/C and Pd/C.

By hydrogenation an octahydro biquinoline compound of general formula (XV) is formed

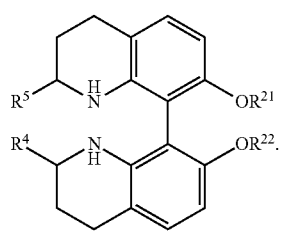

(XV)

Groups $R^{21}$ and $R^{22}$ may then in some embodiments be converted to the corresponding moieties $R^2$ and $R^3$ as defined above, using standard synthesis techniques available in the art. Other groups than H (proton) at the positions of $R^1$ of formula (V) may then be introduced by standard techniques in the art. The secondary amine of the cyclic octahydro biquinoline structure may be converted to a tertiary amine by a reaction with an alkyl halide, an alkyl cyanide or with a diazo compound.

In some embodiments where $R^{21}$ and $R^{22}$ differ from hydrogen, they may be hydrolysed, thereby converting them to hydrogen. Other groups than H (proton) at the positions of $R^2$ and $R^3$ of formula (V) may then be introduced by standard techniques in the art. A hydroxyl group that includes $R^2$ and $R^3$ of formula (V) may be converted to an ether by a reaction with an alkyl halide, a diazo compound or transetherification using an ether compound, or to an ester by a reaction with a carboxylic acid, a carboxylic acid halide or transesterification using an ester compound. Those skilled in the art will be aware of the reactivities of the two respective groups (i.e. amine vs. hydroxyl group) that may require the use of protective groups for the synthesis of certain combinations of $R^1$, $R^2$, $R^3$, $R^4$ and $R^5$.

Similar to BINOL, the octahydro biquinoline compound (V) is axially chiral. Accordingly, the two enantiomers (Va) and (Vb), illustrated above, exist. Compound (V) can thus exist in racemic form or in enriched or pure enantiomers. The stereochemistry of the respective compound may be analysed according to any method known in the art, such as for instance 2D-NMR based on homo- or heteronuclear J-coupling values (Riccio, R., et al., Pure Appl. Chem. (2003) 75, 2-3, 295-308), electron ionisation mass spectrometry, polarimetry, circular dichroism spectroscopy (e.g. using the split Cotton-effect based on the Davydov splitting, see e.g. Allemark, S. G., Nat. Prod. Rep. (2000) 17, 145-155), enantioselective chromatography, derivatisation in combination with standard analytical techniques such as NMR, including any suitable 2D-NMR technique, for example based on the nuclear Overhauser effect, as well as X-ray crystallography or solid state NMR (see e.g. Harper, J. K., et al., J. Org. Chem. (2003) 68, 46094614). The term "enriched" in the context of enantiomers refers to a mixture of enantiomers in which one enantiomer is present in excess when compared to the other enantiomer, which may be conveniently expressed in terms of enantiomeric excess.

Enantiomers have identical properties in a symmetrical environment, albeit their properties may differ in an unsymmetrical environment. For this reason a single enantiomer of compound of formula (V), i.e. (Va) or (Vb), similar to BINOL may, by providing an unsymmetrical environment, convey asymmetric induction. The compound of formula (V) is therefore particularly useful in asymmetric synthesis, e.g. stereoselective synthesis. For the same reason enantiomers, having identical physical properties, cannot be separated without the use of further chiral moieties. Where more than a pair of enantiomers exist, typically due to the presence of more than one chiral center, however, diastereomers are provided, which have similar, but not identical physical characteristics. The present inventors have identified a corresponding method of separating a mixture of enantiomers of formulae (Va) and (Vb). Thus, the present invention provides enriched as well as at least essentially pure enantiomers of compound (V). Each of the enantiomers may be provided in an enantiomeric excess of at least 60% ee, at least 70% ee, at least 80% ee, at least 85% ee, at least 90% ee, at least 94% ee, at least 96% ee, at least 97% ee, at least 98% ee, at least 98.5% ee, at least 99% ee, at least 99.5% ee or at least 99.9% ee.

The separation of enantiomers of formulae (Va) and (Vb) according to the present invention, i.e. of the enantiomers,

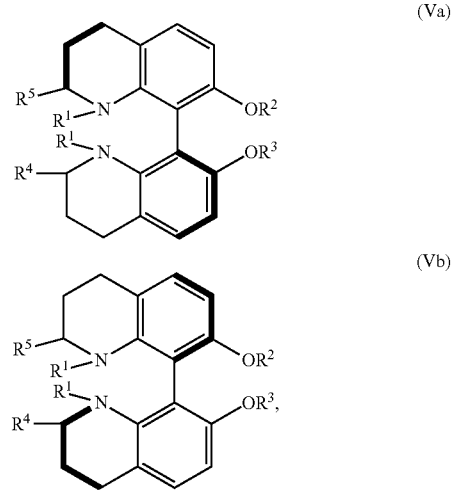

(Va)

(Vb)

is carried out by reacting the compound of formula (V), which may typically be provided as a mixture of compounds (Va) and (Vb), with an enantiomer of Menthyl chloroformate. Thereby a diastereomeric monomenthyl carbonate of Formula (VIII) is formed

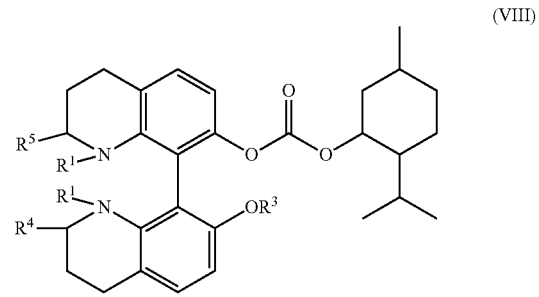

(VIII)

As an illustrative example, the enantiomer of Menthyl chloroformate may be (1R)-(−)-Menthyl chloroformate. In this case the diastereomeric monomenthyl carbonate of Formula (VIII) is of the formula (VIII')

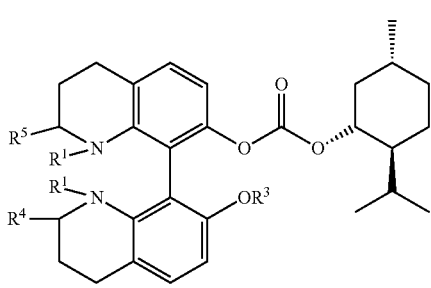

Accordingly, each of compounds (Va) and (Vb) is converted into a corresponding diastereomer. The present inventors have surprisingly found that none of the other tested diastereomers, obtained with chiral compounds that were reacted with compound (V), could be separated into individual diastereomers. However, the obtained compounds (VIIIa) and (VIIIb), following reaction with Menthyl chloroformate, can conveniently be separated:

(VIIIa)

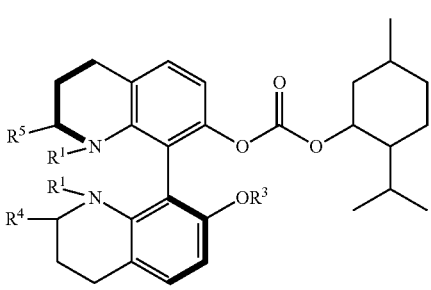

(VIIIb)

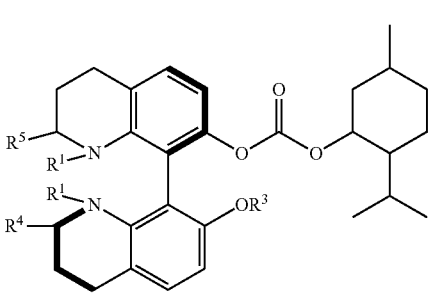

Thus, for instance the obtained compounds (VIIIa) and (VIIIb) that were of the formulas

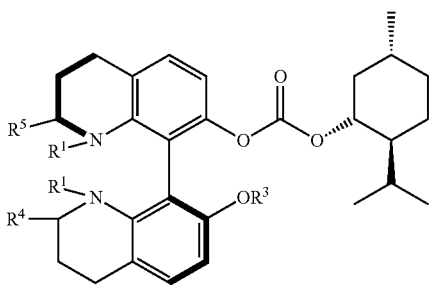

-continued

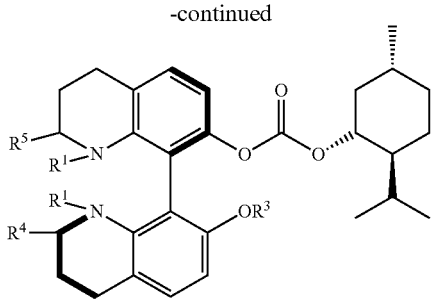

could be conveniently isolated, thereby separating them from each other. Isolation may for example be achieved using chromatographic techniques or based on differential solubility. The latter may be used in a separation by fractional crystallisation, typically including recrystallisation.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognised that various modifications are possible within the scope of the invention claimed. Additional objects, advantages, and features of this invention will become apparent to those skilled in the art upon examination of the following examples thereof, which are not intended to be limiting. Thus, it should be understood that although the present invention is specifically disclosed by exemplary embodiments and optional features, modification and variation of the inventions embodied therein herein disclosed may be resorted to by those skilled in the art, and that such modifications and variations are considered to be within the scope of this invention.

In order that the invention may be readily understood and put into practical effect, particular embodiments will now be described by way of the following non-limiting examples.

EXAMPLES

General Methods

Experiments involving moisture and/or air sensitive components were performed in oven-dried glassware under a positive pressure of nitrogen using freshly distilled solvents. Commercial grade solvents and reagents were used without further purification with the following exceptions: Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography was performed using Merck silica gel 60 with freshly distilled solvents. Columns were typically packed as slurry and equilibrated with the appropriate solvent system prior to use.

Infrared spectra were recorded on a Bio-Rad FTS 165 FTIR spectrometer. The oil samples were examined under neat conditons. High Resolution Mass (HRMS) spectra were obtained using Finnigan MAT95XP GC/HRMS (Thermo Electron Corporation).

Proton nuclear magnetic resonance spectra ($^1$H NMR) were recorded on a Bruker Avance DPX 300 and Bruker AMX 400 spectrophotometer (CDCl$_3$ as solvent). Chemical shifts for $^1$H NMR spectra are reported as δ in units of parts per million (ppm) downfield from SiMe4 (δ 0.0) and relative to the signal of chloroform-d (δ 7.2600, singlet). Multiplicities were given as: s (singlet); d (doublet); t (triplet); q (quartet); dd (doublets of doublet); ddd (doublets of doublets of doublet); dddd (doublets of doublets of doublets of doublet); dt (doublets of triplet); or m (multiplets). The number of protons (n) for a given resonance is indicated by nH. Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.0, triplet). The proportion of diastereomers and geometric isomers was determined from the integration of $^1$H NMR and $^{13}$C NMR spectra.

Enantioselectivities were determined HPLC analysis employing a Daicel Chiracel column at 25° C. Optical rotation was measured using a JASCO P-1030 Polarimeter equipped with a sodium vapor lamp at 589 nm. Concentration is denoted as c and was calculated as grams per deciliters (g/100 mL) whereas the solvent. Absolute configuration of the products was determined by comparison with known compounds. X-ray crystallogphy analysis was performed on Bruker X8 APEX X-Ray diffractometer. The synthesis of compound 2, 3, 4 see Blakemore, P R, Kilner, C, Milicevic, S D, *J. Org. Chem.* (2005) 70, 373).

Figure 1B:
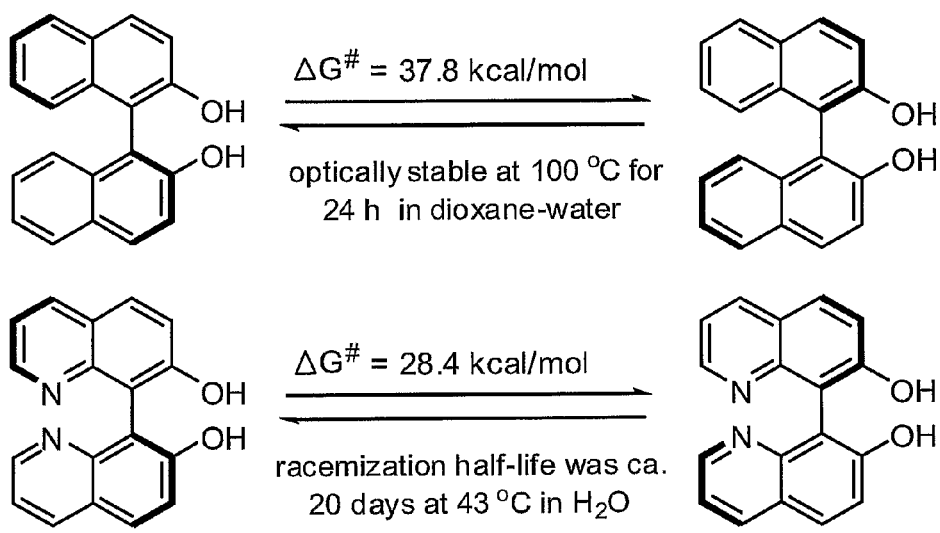
FIG. 1B illustrates as a comparison the configurational stabilities of BINOL and the corresponding aza analogue.
Figure 1C:
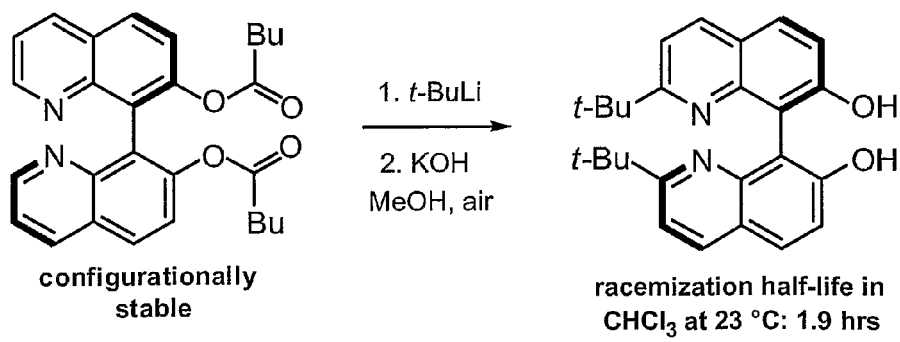
FIG. 1C illustrates that even if $R^4$ and $R^5$ are sterically large (cf. Blakemore, P R, et al., J Org Chem (2007) 9368), a 8,8'-biquinolyl compound as depicted in the center of the FIG. 1 is racemizing rapidly. Only if sterically large moieties $R^2$ and $R^3$ are used, can racemisation be avoided.
Figure 2:
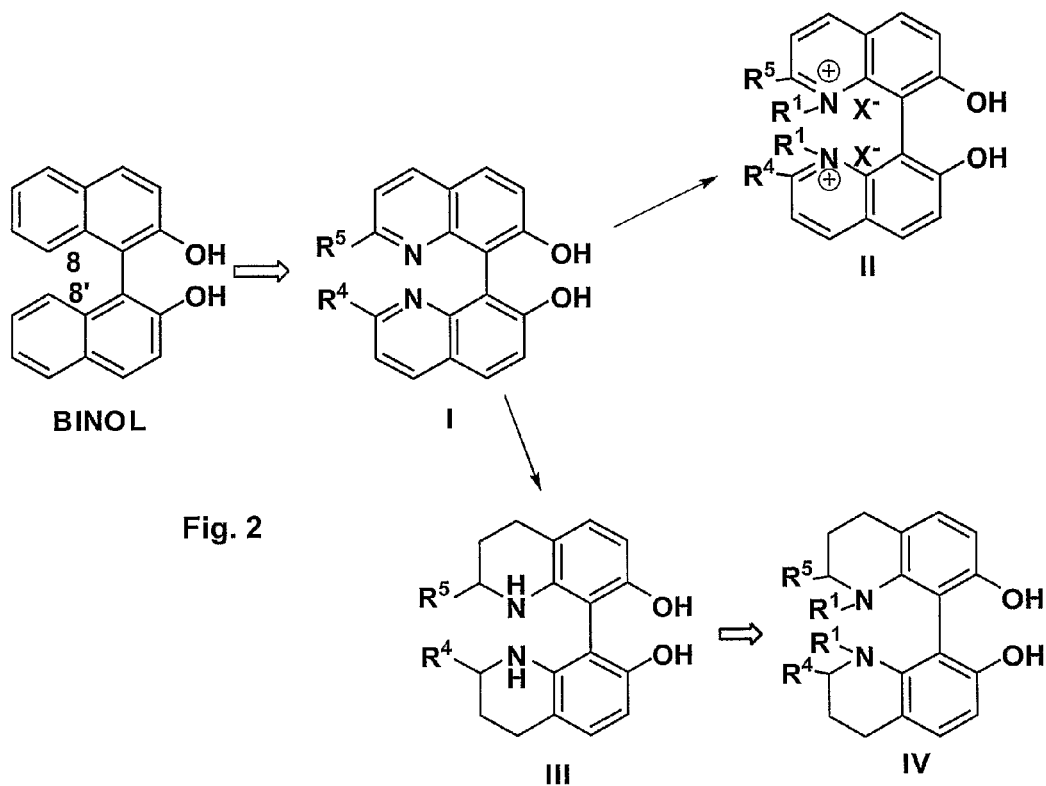
FIG. 2 depicts schematically the design of a bifunctional ligand according to the invention, wherein I can be taken to define an aza analogue of BINOL if $R^4$ is H.

Previous attempts of introducing a heteroatom into 8,8'-positions by a sp$^2$-hybridized N-atom were discouraging since it was observed that the resulting bifunctional 7,7'-dihydroxy-8,8'-biquinolyl I was not configurationally stable to serve as a chiral ligand (cf. FIG. 1 and FIG. 2; Blakemore, P R, et al., Org. Chem. (2005) 70, 373; Blakemore, P R, et al., J. Org. Chem. (2006) 71, 8212; Blakemore, P R, et al., J. Org. Chem. (2007) 72, 9368). Furthermore, its high polarity and insolubility in common organic solvents limited its application in asymmetric catalysis. The invention resolves this problem by providing stable ligand IV, which can serve as a chiral ligand for asymmetric synthesis instead of I. Experimental data on a route to compound II showed that alkylation of the sp$^2$-hybridized groove N-atom was difficult. A synthesis as well as chiral resolution of the new bifunctional ligand IV was then developed, which is configurationally stable to serve as a new chiral ligand for asymmetric catalysis. Without being bound by theory, it is believed that the octahydro biquinolyl part of IV induces considerably electronic perturbation and steric tuning as an aza analogue of 1,1'-binaphtyl-2,2'-diol (BINOL, FIG. 2).

Figure 3:
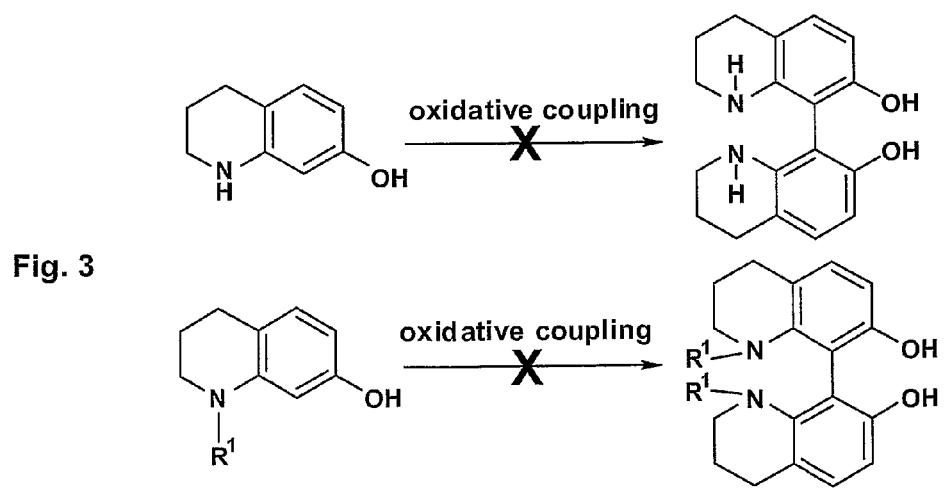
FIG. 3 illustrates the failure of oxidative coupling.

Initial attempts to synthesize the target molecule III or IV (cf. FIG. 2) by various direct oxidative coupling reactions of 7-tetrahydroquinolinol or 1-methyl-7-tetrahydroquinolinol were unsuccessful (FIG. 3). The common single-electron oxidants methods tested are as follows: CuCl(OH).TMEDA (Noji, M, et al., Tetrahedron Lett. (1994) 35, 7983); CuCl$_2$BnNH$_2$ (Vyskocil, S, et al., J. Org. Chem. (2001) 66, 1359) FeCl$_3$: (Ding, K, et al., Tetrahedron (1996) 52, 1005); (NH$_4$)$_2$Ce(NO$_3$)$_6$: (Jiang, P, & Lu, S, Synth. Commun. (2001) 31, 131).

Figure 4A:
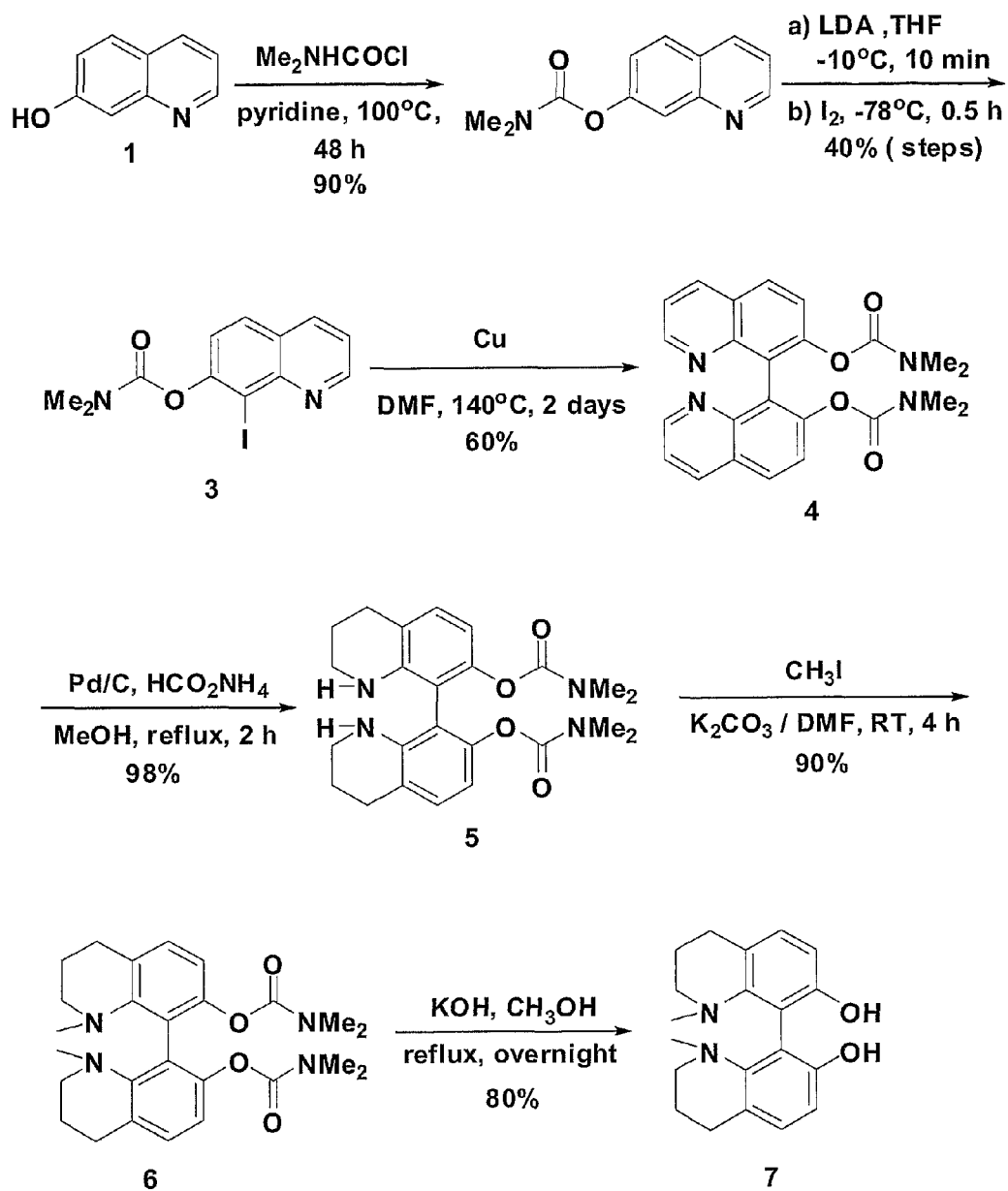
FIG. 4A depicts the synthesis of the bifunctional chiral ligand 1,1'-dimethyl-octahydro-8,8'-biquinoline-7,7'-diol (7).

Without being bound by theory, failure of the coupling reactions is believed to arise from the poisoning of the metal by the basic nitrogen atom. Accordingly the established Ullmann coupling strategy was selected as an alternative way to construct the biaryl system. When MeI was used to conduct methylation of 4, only trace of mono methylation product was observed. Under microwave conditions, the messy complex was formed. This condition is to be further optimized. Starting from the 7-hydroxyquinoline, under the protection of dimethylaminocarbonyl chloride to give carbamate 2 in 90% yield. Direct ortho metalation of carbamate 2 was carried out with LDA in THF at −78° C., after which a solution of iodine in THF was added to the resulting metalate at −78° C. to afford 8-iodoquinoline 3 in 40% yield. Ullmann coupling of iodide 3 with copper catalyst proceeded in 60% yield to produce biaryl 4. The quinoline part of 4 was effectively reduced to give biquinolyl 5 quantitatively in the presence of ammonium formate and Pd/C. Methylation of the amine ensured using potassium carbonate as base, and finally culminating at basic methanolysis of the carbamate groups of 5 to afford the target molecule 7 in good yield (FIG. 4).

Compound 7 was observed to be less polar than II and exhibited good solubility in a wide range of common organic solvents such as CH$_2$Cl$_2$, CHCl$_3$ and THF which evaded the solubility problem for future application. An X-ray crystallographic analysis of 7 provided definitive proof of the structure and revealed a preferred transoid conformation with the angle between the two aromatic ring planes being 124.97°. In comparison, the angle between the two quinolyl ring planes of racemic II as its dimethanol solvate is 104.5°, and racemic BINOL is only slightly transoid in the solid state (angle between naphthyl ring planes is 91.4°). In 7, N . . . H—O contact distances for intramolecular hydrogen bonds are 1.84 and 0.9 Å.

Preparation of 1,1',2,2',3,3',4,4'-octahydro-8,8'-biquinoline-7,7'-diyl bis(dimethylcarbamate) (5)

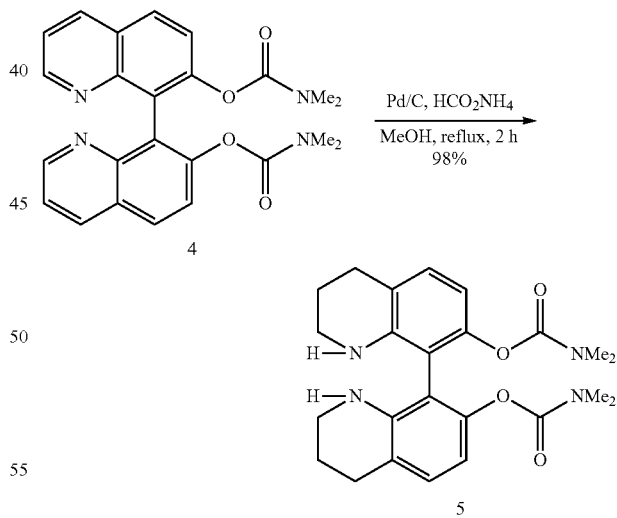

To an oven dried round-bottom flask was added 4 (2.0 g, 4.65 mmol), Pd/C (0.25 g, 2.33 mmol), HCO$_2$NH$_4$ (14.64 g, 232.4 mmol) and MeOH (50 mL). The mixture was heated at 80° C. under N$_2$ for 2 h with stirring and allowed to cool to room temperature. After filtration with celite, the filtrate was concentrated in vacuo and CH$_2$Cl$_2$ was added, washed by saturated NaHCO$_3$ solution and brine, and dried over anhydrous magnesium sulfate, filtered and concentrated in vacuo. The residue was further purified by column chromatography (eluting with EtOAc/Hexane=1:1) to yield 5 (1.99 g, 98%) as a pale yellow solid.

Rf=0.27 (EA:Hexane=1:4);

$^1$H NMR (300 MHz, CDCl$_3$) δ 6.90 (2H, d, J=8.1 Hz), 6.44 (2H, d, J=8.1 Hz), 3.96 (2H, s), 3.25-3.08 (4H, m), 2.77-2.71 (10H, m), 2.62 (4H, s), 1.97-1.84 (2H, m), 1.82-1.70 (2H, m);

$^{13}$C NMR (75 MHz, CDCl$_3$) δ 154.9, 148.1, 144.1, 128.5, 118.1, 110.7, 109.1, 41.6, 35.7), 34.0, 27.0, 21.7;

FTIR (KBr, neat): v 721, 1377, 1458, 2853, 2924, 2953, 3422 cm$^{-1}$;

HRMS (ESI) calcd. for C$_{24}$H$_{30}$N$_4$O$_4$[M+1]$^+$: 439.2345. found 439.2328.

Preparation of 1,1'-dimethyl-1,1',2,2',3,3',4,4'-octahydro-8,8'-biquinoline-7,7'-diyl bis(dimethylcarbamate) (6)

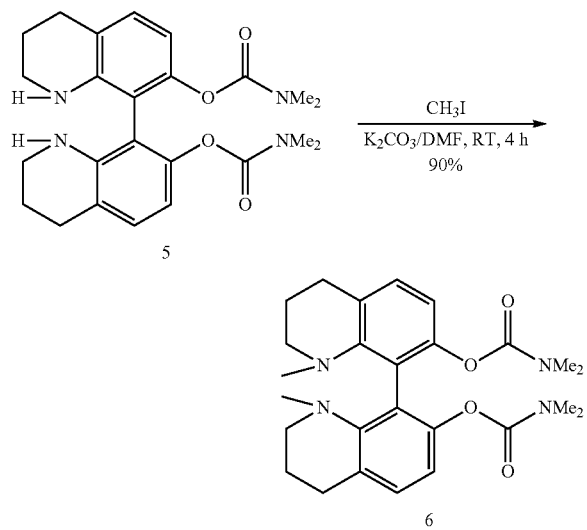

A portion of solid K$_2$CO$_3$ (1.8 g, 13.6 mmol) was added into solution of 5 (2.0 g, 4.56 mmol) in anhydrous DMF. Then CH$_3$I (4 mL, 40 mmol) was added dropwise to the solution over 5 min. The mixture was stirred at room temperature under N$_2$ for 6 h. Then it was quenched with H$_2$O and the aqueous layer was extracted with EtOAc (50 mL×3). The combined organic extracts were washed with H$_2$O and brine, dried over anhydrous magnesium sulfate, filtered and concentrated in vacuo. The residue was further purified by column chromatography (eluting with EtOAc/Hexane=2:1) to yield 6 (1.91 g, 90%) as a pale yellow solid.

R$_f$=0.33 (EA:Hexane=1:4);

$^1$H NMR (300 MHz, CDCl$_3$) δ 6.83 (2H, d, J=8.6 Hz), 6.57 (2H, d, J=8.6 Hz), 2.98-2.92 (2H, m), 2.87 (8H, s), 2.79 (5H, s), 2.76 (5H, s), 2.63-2.57 (10H, m), 2.33 (6H, s), 1.80-1.63 (4H, m) ppm;

$^{13}$C NMR (75 MHz, CDCl$_3$) δ 154.1, 148.4, 146.8, 127.4, 124.0, 118.9, 112.5, 52.2, 41.2, 36.2, 31.1, 28.3, 20.8 ppm;

FTIR (KBr, neat): v 721, 1377, 1458, 2853, 2924, 2953 cm$^{-1}$;

HRMS (ESI) calcd. for C$_{26}$H$_{34}$N$_4$O$_4$[M+1]$^+$: 467.2658. found 467.2636.

Preparation of 1,1'-dimethyl-1,1',2,2',3,3',4,4'-octahydro-8,8'-biquinoline-7,7'-diol (7)

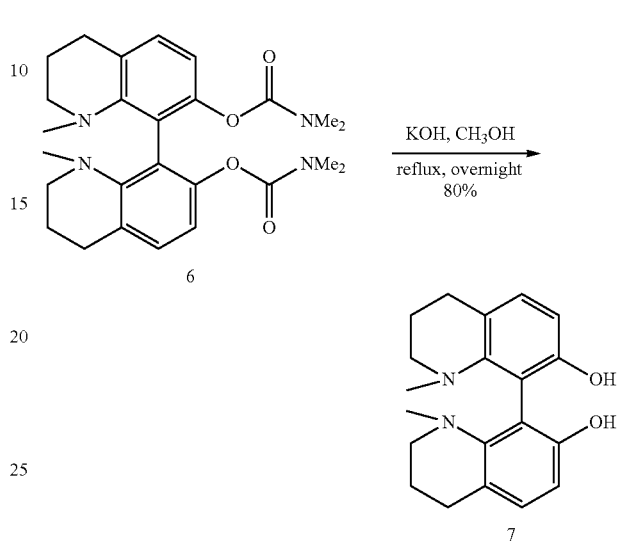

A solution of 6 (2.0 g, 4.29 mmol) in 10 wt. % methanolic KOH (45 mL) was stirred at reflux for 20 h. The resulting solution was allowed to cool to room temperature and concentrated in vacuo. The residue was dissolved in H$_2$O and the pH adjusted to a value of 7 by careful addition of 1 M aq. HCl. The aqueous phase was saturated with NaCl and extracted with EtOAc (50 mL×6). The combined organic extracts were washed with brine, dried over anhydrous magnesium sulfate, filtered and, concentrated in vacuo. The residue was further purified by column chromatography (eluting with EtOAc/Hexane=4:1) to yield 7 (1.09 g, 76%) as a white solid.

R$_f$=0.36 (EA:Hexane=1:4);

$^1$H NMR (300 MHz, CDCl$_3$) δ 10.3 (2H, s), 7.02 (2H, d, J=8.2 Hz), 6.76 (2H, d, J=8.3 Hz), 3.27 (2H, td, J=13.2, 2.3 Hz), 3.10 (2H, dt, J=13.2, 3.7 Hz), 2.86-2.83 (4H, m), 2.52 (6H, s), 2.03-1.90 (2H, m), 1.85-1.75 (2H, m);

$^{13}$C NMR (75 MHz, CDCl$_3$) δ 154.5, 144.2, 130.4, 120.9, 120.0, 115.4, 51.8, 42.2, 27.6, 17.2.;

FTIR (KBr, neat): v 721, 1377, 1456, 1634, 2853, 2922, 2953, 3420, 3445 cm$^{-1}$;

HRMS (ESI) calcd. for C$_{20}$H$_{24}$N$_2$O$_2$ [M+1]$^+$: 325.1916. found 325.1902.

With an efficient synthesis of 7 established, its resolution was next explored. We found that the general method by fractional crystallization of diastereomeric mixtures of salts or complexes formed with various chiral complexation reagents such as N-benzylcinchonidinium chloride and trans-1,2-diaminocyclohexane was unsuccessful (Wang, Y, et al., Tetrahedron (2000) 56, 4447; Schanz, H J, et al., Tetrahedron: Asymmetry (2003) 14, 2763). Without being bound by theory, this initial failure implied that lower acidity of phenol groups rendered hydrogen bonding formation with chiral reagents more difficult as the piperidine unit made the aromatic rings more electron-rich.

Among the chromatographic resolutions tactics for the resolution of BINOL-like molecules, the chromatographic separation of diastereomeric bismenthyl carbonate derivatives has proven to be particularly useful (for resolution of BINOL through separation of the bis[(−)-menthoxycarbonyl] derivatives, see: Fabbri, D, et al., J. Org. Chem. (1995) 60, 6599). When excess of (+)-menthyl chloroformate was employed in the presence of triethylamine at room temperature, bismenthyl carbonates and monocarbonate were obtained simultaneously.

However, different from the previous report (Fabbri et al., 1995, supra), the bismenthyl carbonate can't be resolved by fractional recrystallization or column chromatography. However, the present inventors found that the monomenthyl carbonate 8 could be separated by column chromatography (FIG. 7). Significant chemical shift differences were observed in the ¹H NMR (FIG. 14).

Figure 6:
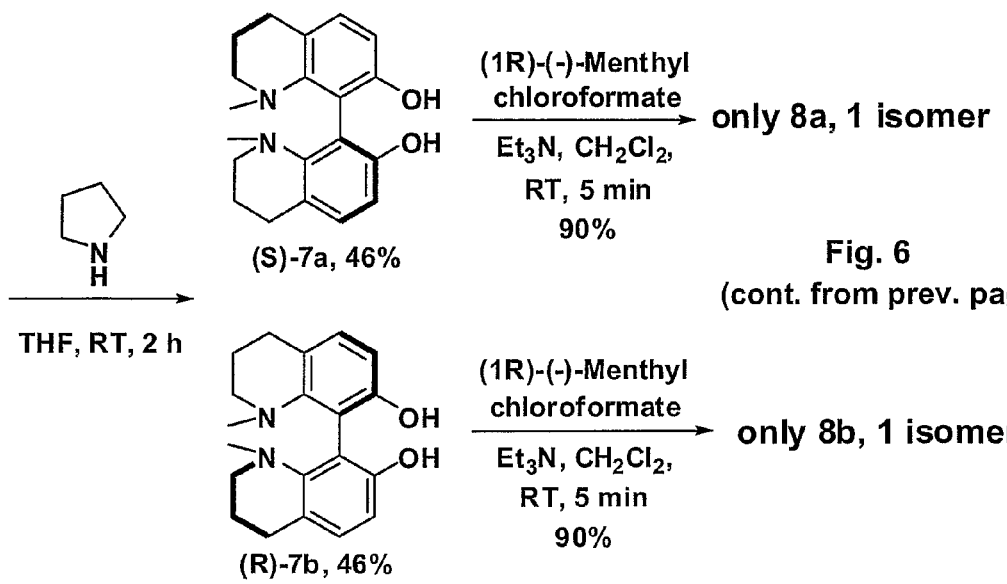
FIG. 6 depicts the resolution of the obtained chiral ligands and their configuration determination.

For the menthyl moiety in 8a and 8b, the C-1 proton appears as a triplet at δ 4.37 ppm and 4.28 ppm significant difference as a doublet at δ 0.70 ppm and 0.83 ppm respectively. The less polar diastereoisomer 8a was determined by X-ray crystallographic analysis (FIG. 6). It was assigned to possess an (S)-configuration relating it to the configuration of (1R,2S,5R)-menthyl moiety. The dihedral angel is 120.16°, N . . . H—O contact distances for intramolecular hydrogen bonds are 1.95 and 0.84 Å. Clean removal of chiral auxiliary groups from 8a and 8b was achieved with pyrrolidine in THF at room temperature. (S)-7a and (R)-7b was obtained in good yield respectively. To determine the enantiomeric excess, reinstallation of menthyl carbonate units onto samples of freshly prepared enantioenriched (S)-7a or (R)-7b gave the corresponding 8a or 8b as single diastereoisomer to reveal that ≥99% e.e. was obtained for each enantiomer. This issue was further confirmed by chiral HPLC (Chiralpak OD-H column, hexane/2-propanol 95:5, 1 mL/min) to afford a single peak in each case for (S)-7a or (R)-7b with retention times of 17.7 and 20.7 min respectively. Each enantiomer has been stored at room temperature for several months without any drop in its enantiopurity.

Figure 4B:
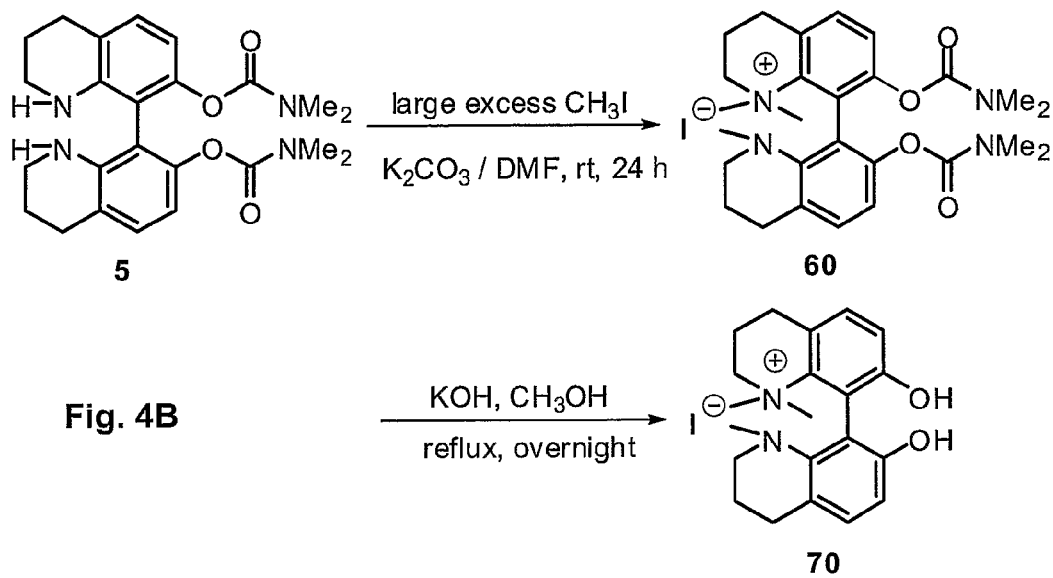
FIG. 4B depicts the synthesis of chiral ionic ligand 70.

When the methylation of 5 was conducted using large excess of iodomethane, the ionic intermediate 60 was obtained in moderate yield without optimization. As a result, the interesting ionic ligand 70 was in hand after deprotection, which provided a unique chiral ionic liquid candidate for future investigations, considering the on-going exploration of chiral ionic liquids and chiral salts in asymmetric catalysis (FIG. 4B).

Preparation of (S)-7'-hydroxy-1,1'-dimethyl-1,1',2,2', 3,3',4,4'-octahydro-8,8'-biquinolin-7-yl(1R,2S,5R)-2-isopropyl-5-methylcyclohexyl carbonate 8a

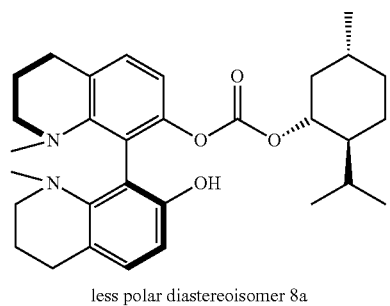

less polar diastereoisomer 8a

To an oven dried round-bottom 10 mL flask equipped with a magnetic stirring bar was added racemate ligand 7 (300 mg, 0.92 mol), CH₂Cl₂ (5 ml) and Et₃N (0.17 mL, 1.1 mmol). Then (−)-menthyl chloroformate (0.24 mL, 1.1 mmol) was added to the solution with stirring. The reaction mixture was stirred for 0.5 h and quenched with water. The aqueous layer was extracted with DCM (3×5 mL), and the combined organic layers were washed with brine (10 mL) and dried over anhydrous Na₂SO₄, filtered and concentrated in vacuo. The residue was purified via column chromatography (eluting with EtOAc/Hexane=5:1) to afford 8a as colorless solid in 38% yield and 8b as colorless oil in 38% yield.

$R_f$=0.31 (EA:Toluene=1:10);

$[\alpha]_D^{20}$=−97.4 (c=1.4, CH₂Cl₂);

¹H NMR (400 MHz, CDCl₃) δ 9.18 (1H, s), 7.07 (1H, d, J=8.4 Hz), 6.84 (2H, dd, J=11.2, 8.1 Hz), 6.41 (1H, d, J=8.1 Hz), 4.37 (1H, td, J=11.0 Hz), 3.22-3.10 (3H, m), 2.98-2.91 (1H, m), 2.89-2.84 (2H, m), 2.69 (3H, s), 2.64 (2H, m), 2.33 (3H, s), 2.01-1.90 (3H, m), 1.81-1.79 (2H, m), 1.63-1.60 (4H, m), 1.31-1.25 (1H, m), 1.05-0.95 (3H, m), 0.88 (3H, d, J=6.6 Hz), 0.83 (3H, d, J=7.0 Hz), 0.63 (3H, d, J=6.9 Hz);

¹³C NMR (100 MHz, CDCl₃) δ 154.5, 153.1, 147.8, 147.3, 144.9, 129.7, 129.4, 126.8, 126.0, 120.1, 117.1, 112.0, 108.7, 52.6, 51.6, 47.1, 41.6, 41.4, 40.6, 34.0, 31.4, 28.7, 27.5, 25.5, 23.0, 22.0, 21.3, 21.0, 16.9, 16.0;

FTIR (KBr, neat): ν 721, 1377, 1456, 1634, 2853, 2922, 2953, 3420, 3445 cm⁻¹;

HRMS (ESI) calcd. for C₃₁H₄₂N₂O₄ [M+1]⁺: 507.3223. found 507.3222.

(R)-7'-hydroxy-1,1'-dimethyl-1,1',2,2',3,3',4,4'-octahydro-8,8'-biquinolin-7-yl (1R,2S,5R)-2-isopropyl-5-methylcyclohexyl carbonate 8b

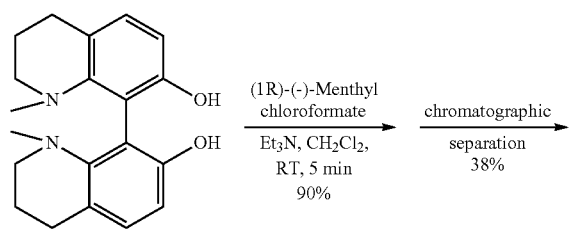

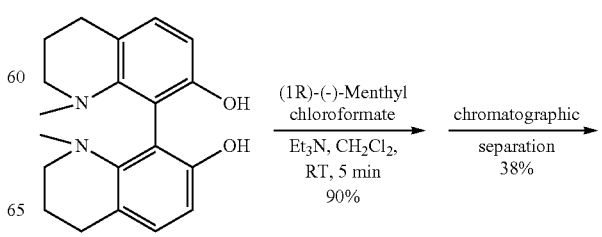

-continued

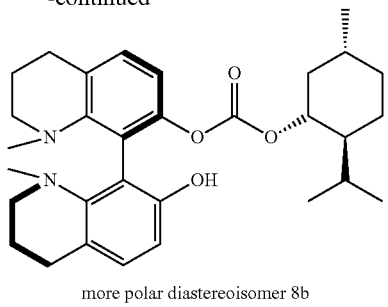

more polar diastereoisomer 8b $R_f$=0.23 (EA:Toluene=1:10);
$[\alpha]_D^{20}$=+47.8 (c=0.9, $CH_2Cl_2$);
$^1$H NMR (400 MHz, $CDCl_3$) δ 9.21 (1H, s), 7.07 (1H, d, J=8.4 Hz), 6.84 (2H, dd, J=11.2, 8.1 Hz), 6.45 (1H, d, J=8.1 Hz), 4.28 (1H, td, J=11.0 Hz), 3.25-3.09 (3H, m), 2.97-2.92 (1H, m), 2.88-2.85 (2H, m), 2.70 (3H, s), 2.69-2.59 (2H, m), 2.33 (3H, s), 2.04-1.89 (3H, m), 1.86-1.78 (2H, m), 1.63-1.60 (4H, m), 1.57 (1H, s), 1.32-1.24 (3H, m), 0.87 (6H, d, J=7.2 Hz), 0.70 (3H, d, J=7.2 Hz);
$^{13}$C NMR (100 MHz, $CDCl_3$) δ 154.5, 153.1, 147.8, 147.3, 144.9, 129.7, 129.4, 126.8, 126.0, 120.1, 117.1, 112.0, 108.7, 52.6, 51.6, 47.1, 41.6, 41.4, 40.6, 34.0, 31.4, 28.7, 27.5, 25.5, 23.0, 22.0, 21.3, 21.0, 16.9, 16.0 ppm;
FTIR (KBr, neat): v 721, 1377, 1456, 1634, 2853, 2922, 2953, 3420, 3445 $cm^{-1}$;
HRMS (ESI) calcd. for $C_{31}H_{42}N_2O_4$ $[M+1]^+$:507.3223. found 507.3222.

Preparation of (S)-1,1'-dimethyl-1,1',2,2',3,3',4,4'-octahydro-8,8'-biquinoline-7,7'-diol

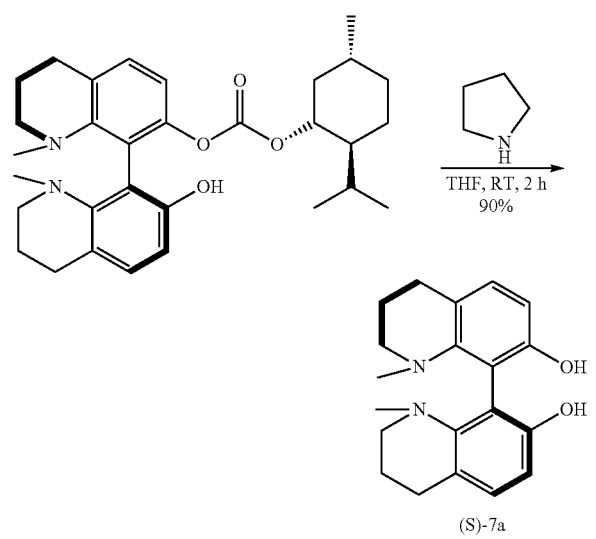

(S)-7a 8a (32.4 mg, 0.1 mmol) was dissolved in 2 mL THF and then 0.1 mL pyrrolidine was added, then the mixture was stirred at room temperature for 2 h, then the solvent was evaporated and the residue was purified via column chromatography (eluting with EtOAc/Hexane=5:1) to afford (S)-7a as colorless solid in 90% yield.
$[\alpha]_D^{20}$=−88.9 (c=6.3, $CH_2Cl_2$);
$R_f$=0.36 (EA:Hexane=1:4);

$^1$H NMR (300 MHz, $CDCl_3$) δ 10.3 (2H, s), 7.02 (2H, d, J=8.2 Hz), 6.76 (2H, d, J=8.3 Hz), 3.27 (2H, td, J=13.2, 2.3 Hz), 3.10 (2H, dt, J=13.2, 3.7 Hz), 2.86-2.83 (4H, m), 2.52 (6H, s), 2.03-1.90 (2H, m), 1.85-1.75 (2H, m);
$^{13}$C NMR (75 MHz, $CDCl_3$) δ 154.5, 144.2, 130.4, 120.9, 120.0, 115.4, 51.8, 42.2, 27.6, 17.2.;
FTIR (KBr, neat): v 721, 1377, 1456, 1634, 2853, 2922, 2953, 3420, 3445 $cm^{-1}$;
HRMS (ESI) calcd. for $C_{20}H_{24}N_2O_2$ $[M+1]^+$: 325.1916. found 325.1902.

Recently, significant progress has been made in the development of chiral Brønsted acid catalysis using BINOL-derived phosphoric acids for enantioselective organic transformations (for leading references, see: Uraguchi, D, & Terada, M, J. Am. Chem. Soc. (2004) 126, 5356; Akiyama, T, et al., Angew. Chem., Int. Ed. (2004) 43, 1566; for recent reviews, see: Akiyama, T, Chem. Rev. (2007) 107, 5744; Doyle, A G, & Jacobsen, E N, Chem. Rev. (2007) 107, 5713; Akiyama, T, et al., Adv. Synth. Catal. (2006) 348, 999; Connon, S J, Angew. Chem. Int. Ed. (2006) 45, 3909; Terada, M, Chem. Commun. (2008) 4097).

Figure 8:
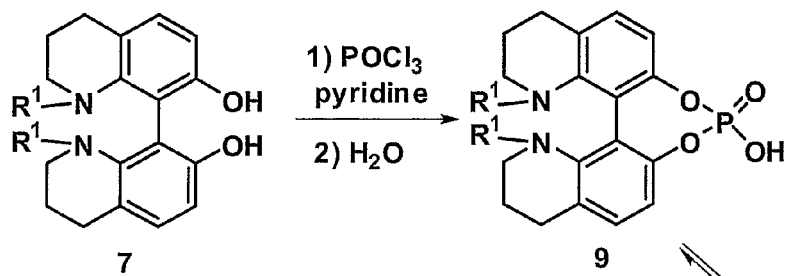
FIG. 8 depicts the formation of the bifunctional catalyst 10.
Figure 9:
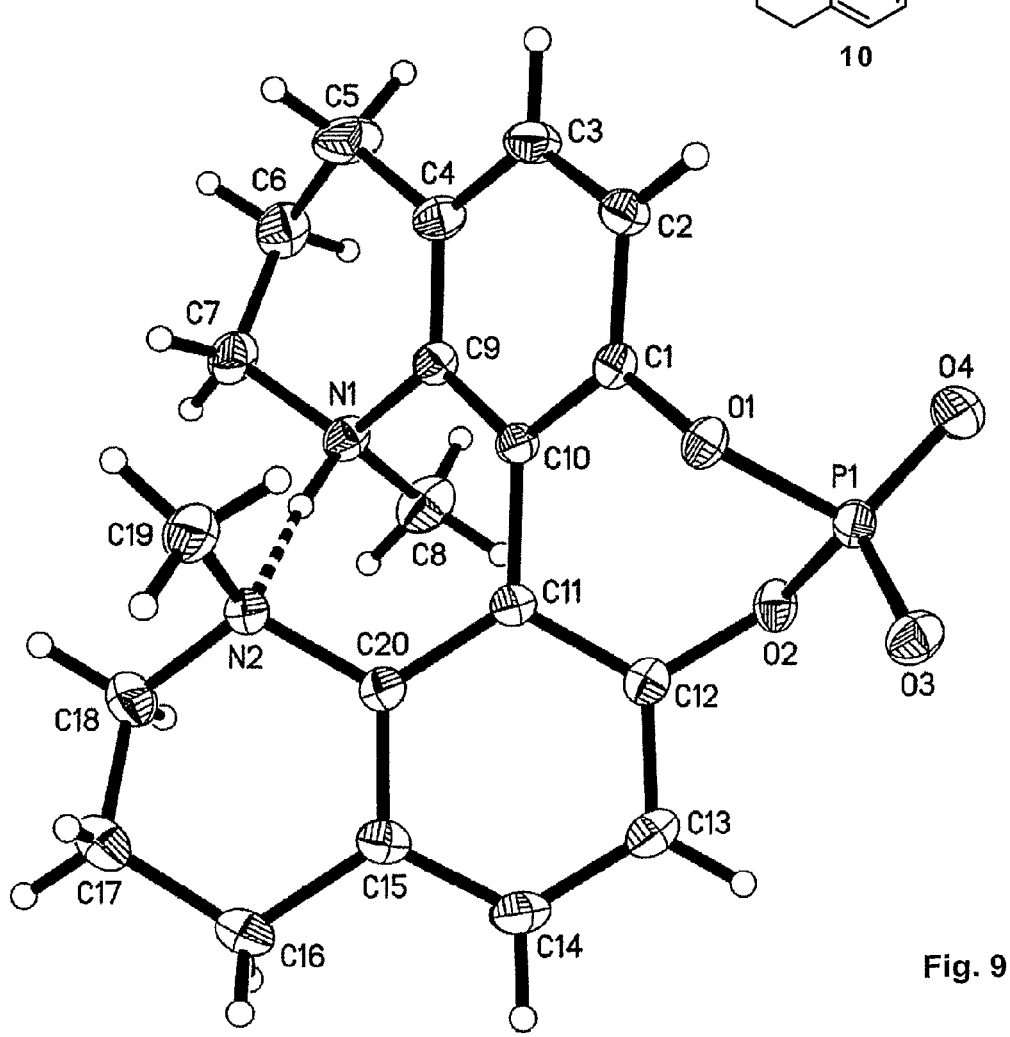
FIG. 9 depicts the X-ray crystal structure of the bifunctional catalyst 10.
Figure 11A:
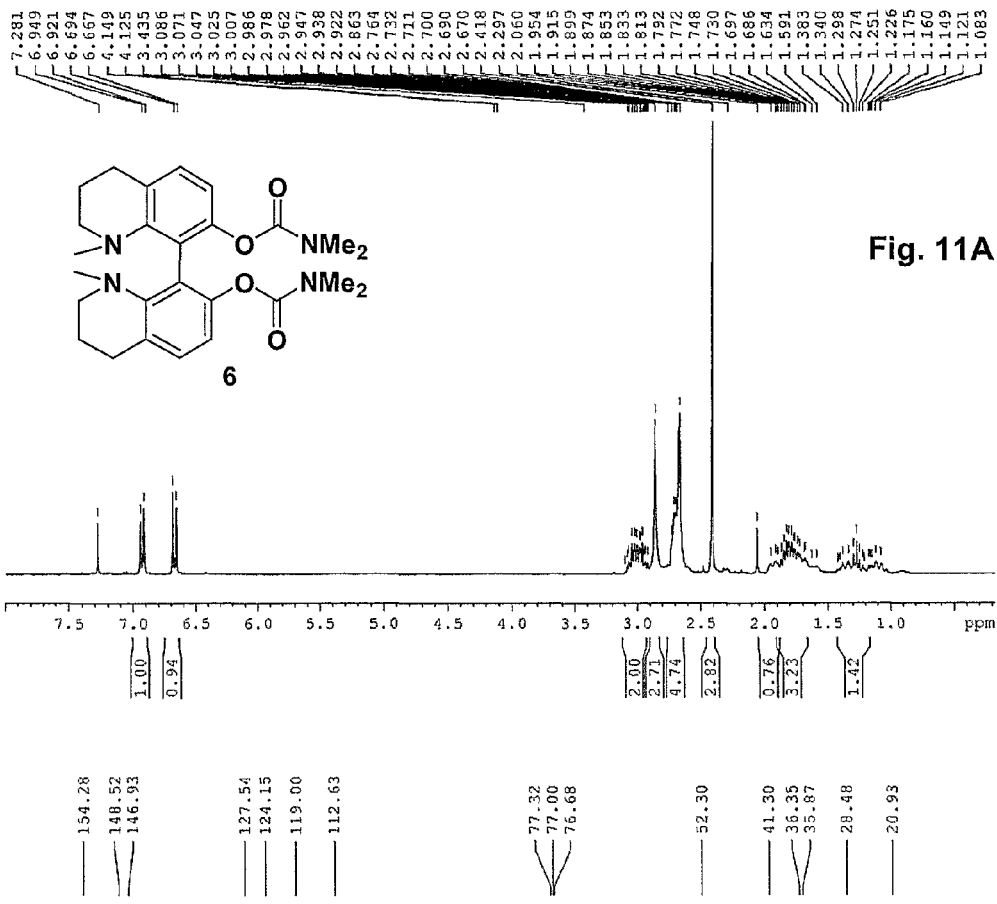
FIG. 11 depicts $^1$H NMR (A) and $^{13}$C NMR (B) spectra of compound 6.
Figure 11B:
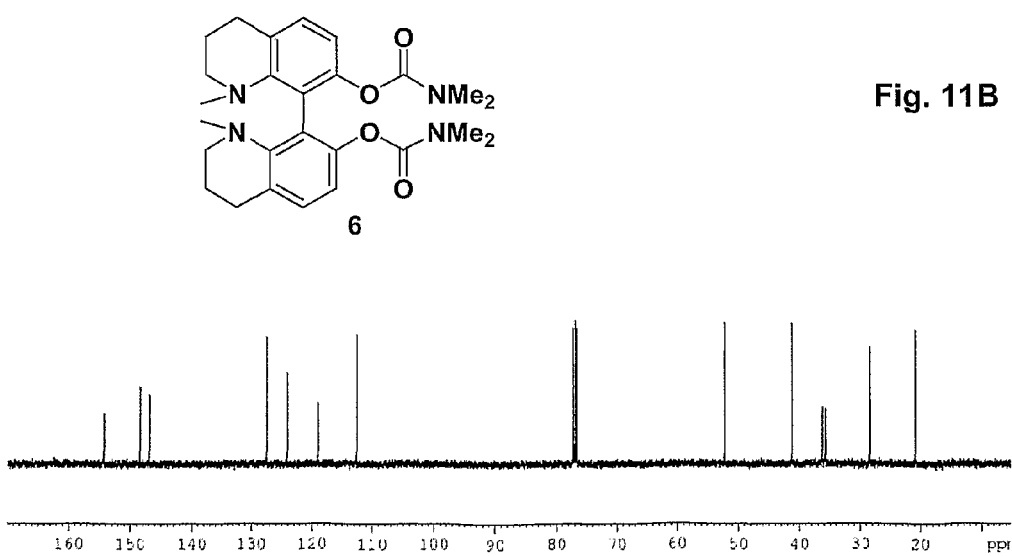
Figure 12A:
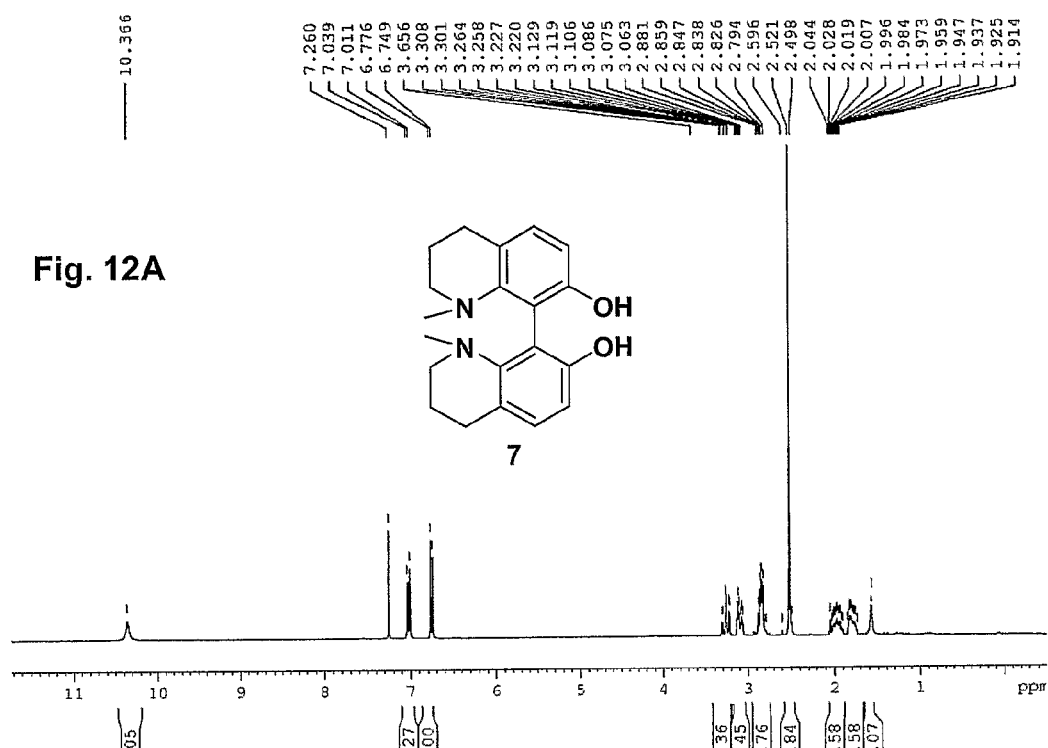
FIG. 12 depicts $^1$H NMR (A) and $^{13}$C NMR (B) spectra of compound 7.
Figure 12B:
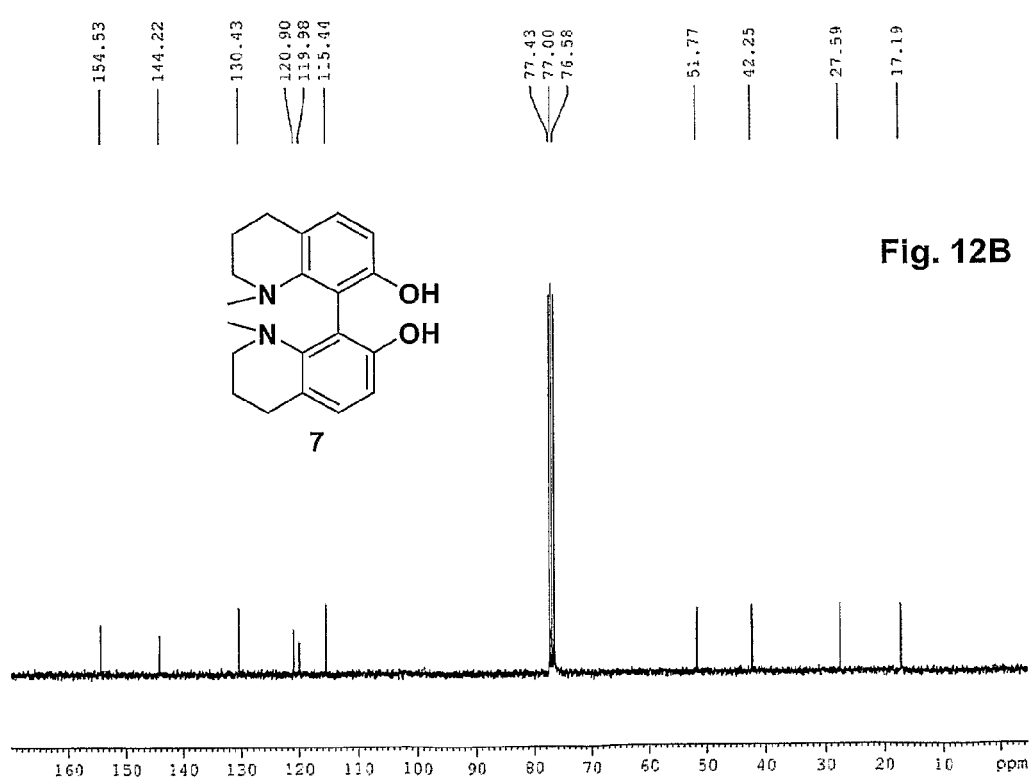
Figure 15A:
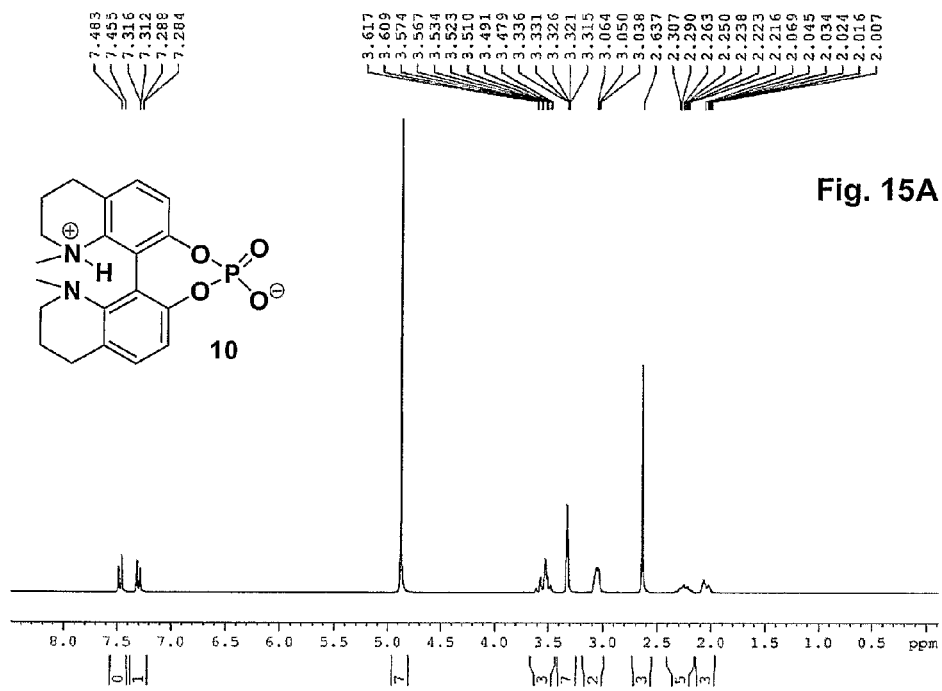
FIG. 15 depicts $^1$H NMR (A) and $^{13}$C NMR (B) spectra of compound 10.
Figure 15B:
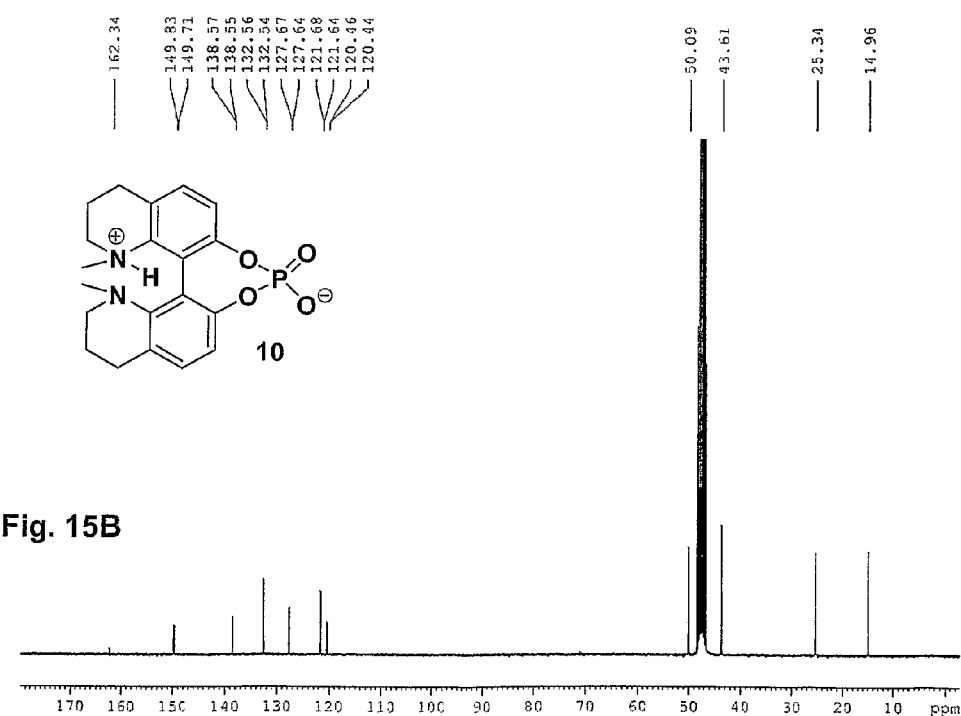

Binol-derived chiral phosphoric acid catalyzed asymmetric reactions always require the modification of the 3,3' position with bulky group to provide steric environment for enantiomeric control as the phosphoric acid generally could only interact with one of the substrate. The inventors envisaged that bifunctional catalyst 9 could interact with the two substrates concurrently, providing an intriguing scaffold for a well defined transition state with its bifunctionality, thus avoiding the chemical complexity of modification of 3,3'-position. So treatment of 7 with phosphoryl chloride in pyridine followed by hydrolysis provided bifunctional catalyst 9 in high yield (FIG. 8). Its crystal structure has been determined which reveals that it exists as zwitterion 10 (FIG. 9). The dihydral angle was 45.96° and the N-methyl group almost was orthogonal to the ring plane due to the strong steric repulsion. This interesting bifunctional catalyst 9 has great potential application in asymmetric catalysis.

Preparation of (R)-1,1'-dimethyl-1,1',2,2',3,3',4,4'-octahydro-8,8'-biquinoline-7,7'-diol

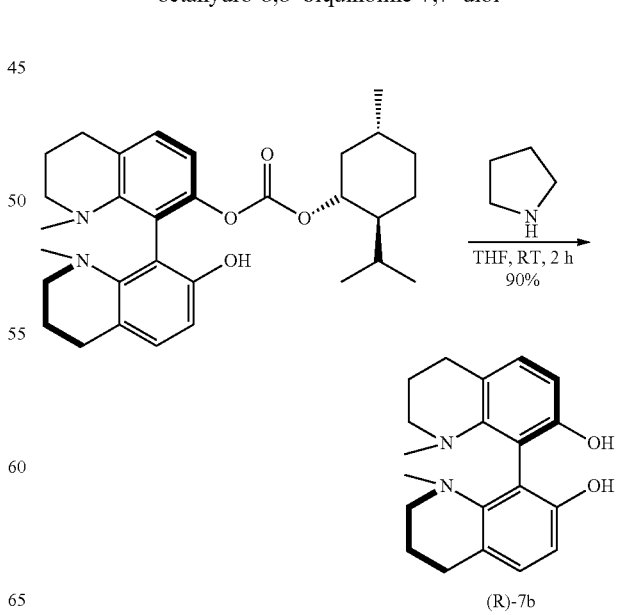

(R)-7b 8b (32.4 mg, 0.1 mmol) was dissolved in 2 mL THF and then 0.1 mL pyrrolidine was added, then the mixture was stirred at room temperature for 2 h, then the solvent was evaporated and the residue was purified via column chromatography (eluting with EtOAc/Hexane=5:1) to afford (R)-7b as colorless solid in 90% yield.

$[\alpha]_D^{20}$=+88.9 (c=6.3, $CH_2Cl_2$);

$R_f$=0.36 (EA:Hexane=1:4);

$^1$H NMR (300 MHz, $CDCl_3$) δ 10.3 (2H, s), 7.02 (2H, d, J=8.2 Hz), 6.76 (2H, d, J=8.3 Hz), 3.27 (2H, td, J=13.2, 2.3 Hz), 3.10 (2H, dt, J=13.2, 3.7 Hz), 2.86-2.83 (4H, m), 2.52 (6H, s), 2.03-1.90 (2H, m), 1.85-1.75 (2H, m);

$^{13}$C NMR (75 MHz, $CDCl_3$) δ 154.5, 144.2, 130.4, 120.9, 120.0, 115.4, 51.8, 42.2, 27.6, 17.2.;

FTIR (KBr, neat): v 721, 1377, 1456, 1634, 2853, 2922, 2953, 3420, 3445 $cm^{-1}$;

HRMS (ESI) calcd. for $C_{20}H_{24}N_2O_2$ [M+1]$^+$: 325.1916. found 325.1902.

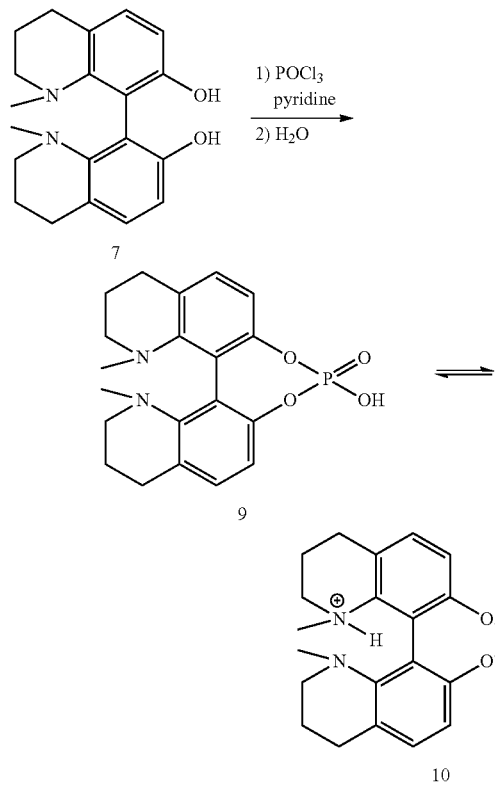

Ligand 7 (67 mg, 0.2 mmol) was dissolved into 1 ml of pyridine under $N_2$ atmosphere. To the resulting solution was added phosphorus oxychloride (1.5-2.0 equiv.) at room temperature and the reaction mixture was stirred for 12 h. Then 1 mL of water was added and the resulting suspension was stirred for additional 30 min. The mixture was were concentrated in vacuo and further purified by column chromatography. The title compound 10 was isolated as white solid in quantitative yield.

$R_f$=0.52 ($CH_2Cl_2$:MeOH=4:1);

$^1$H NMR (300 MHz, $CD_3OD$) δ 7.47 (2H, d, J=8.4 Hz), 7.30 (2H, dd, J=8.4, 1.2 Hz), 3.62-3.48 (4H, m), 3.05 (4H, t, J=4.1 Hz), 2.64 (s, 6H), 2.31-2.22 (2H, m), 2.07-2.01 (2H, m);

$^{13}$C NMR (75 MHz, $CD_3OD$) δ 149.8, 149.7, 138.6, 138.5, 132.6, 132.5, 127.7, 127.6, 121.7, 121.6, 120.5, 120.4, 50.1, 43.6, 25.3, 15.0;

HRMS (ESI) calcd. for $C_{20}H_{24}N_2O_4$ P[M+1]$^+$:387.1474. found 387.1465.

FTIR (KBr, neat): v 756, 1107, 1470, 1599, 1673, 2349, 2951, 3019 $cm^{-1}$.

Figure 7A:
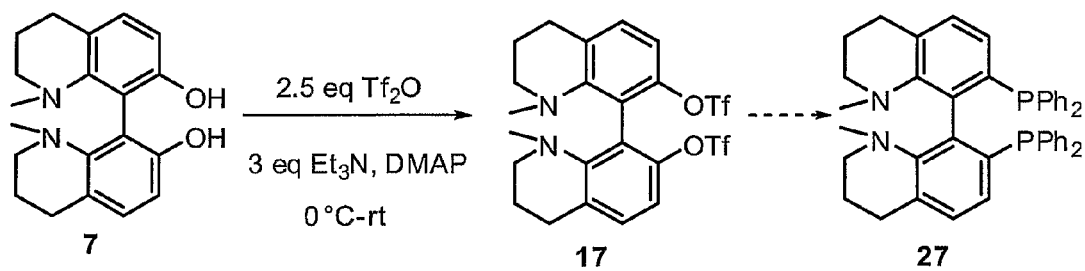
FIG. 7A depicts the synthesis of triflate 17 from 1,1'-dimethyl-octahydro-8,8'-biquinoline-7,7'-diol (7). The triflate may provide a starting point for the synthesis of diphosphine ligand 27.
Figure 7B:
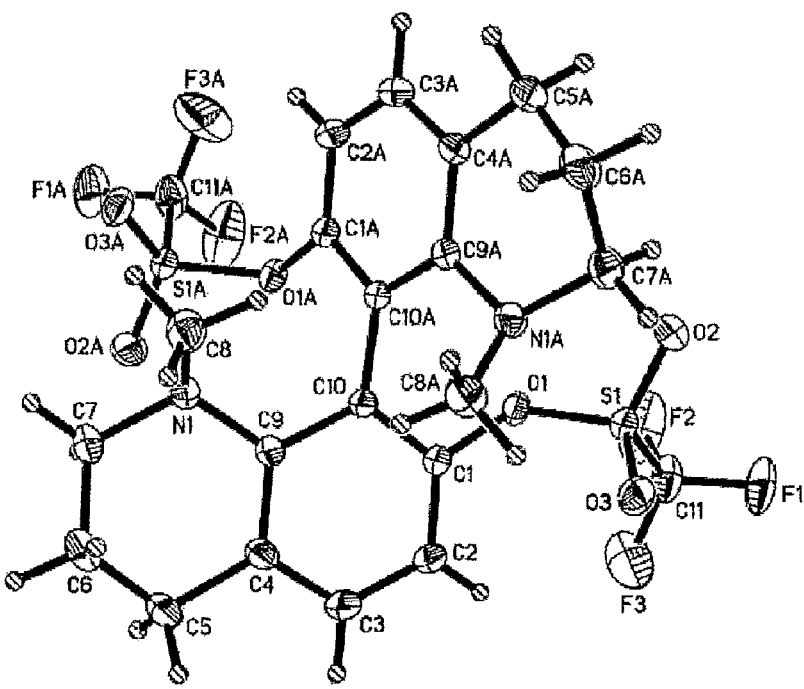
FIG. 7B depicts the crystal structure of triflate 17.

To further explore the application of this new skeleton, treatment of 75 with $Tf_2O$ under base conditions affored triflate 81 (FIG. 7B). Further transformation of 81 to diphosphine ligand 82 could in a preliminary study not yet be achieved (FIG. 7A).

In summary, a new bifunctional ligand 1,1'-dimethyl-octahydro-8,8'-biquinoline-7,7'-diol has been developed as an aza analogue of BINOL. The enantiomers of 1,1'-dimethyl-octahydro-8,8'-biquinoline-7,7'-diol were obtained by chromatographic resolution. The application of the novel ligand in asymmetric catalysis is highly anticipated. This new member of the aza BINOL family will open up new catalyst design and provide synthetic material in many fields such as chiral supramolecular recognition and crystal engineering.

The X-Ray Crystal Data of 7, 8a and 10

1,1'-dimethyl-1,1',2,2',3,3',4,4'-octahydro-8,8'-biquinoline-7,7'-diol (7)

Figure 5A:
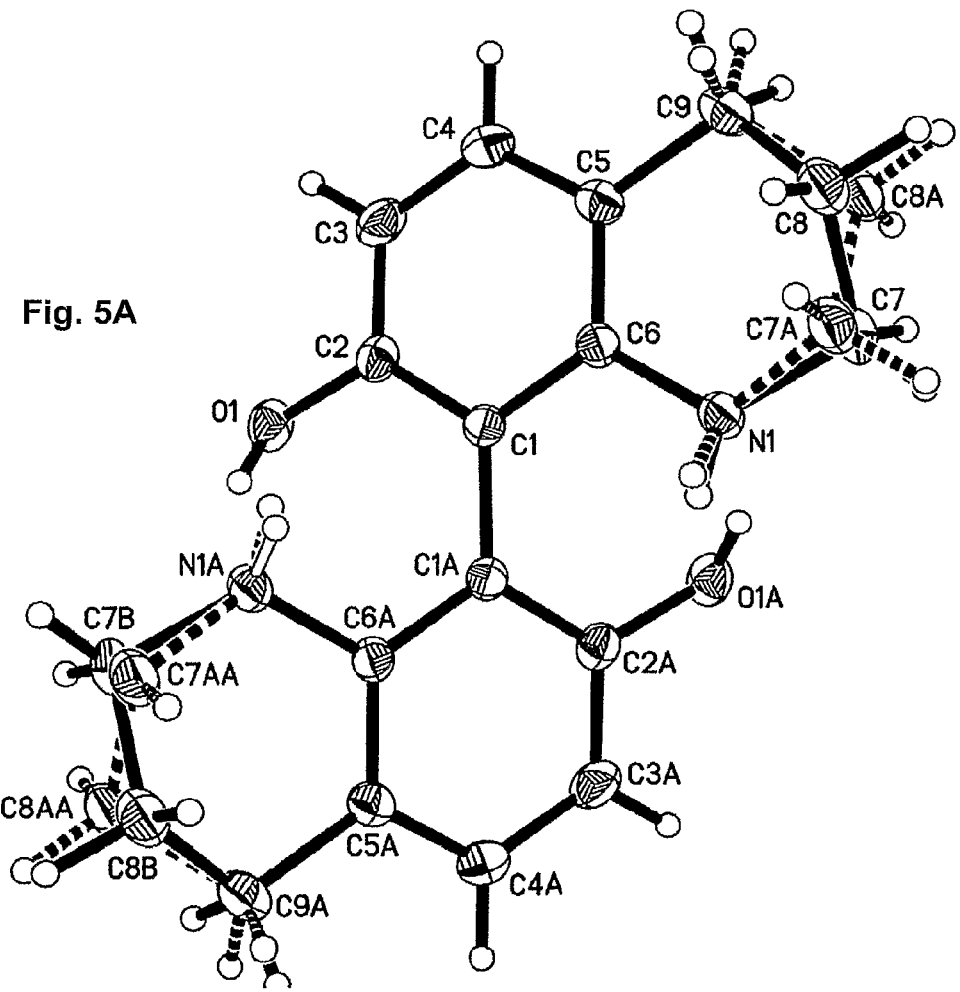
FIG. 5A depicts the X-ray crystal structure of compound 7.

For a graphical representation of the structure of compound 7 see FIG. 5.

Crystal Data and Structure Refinement for Compound 7.

| | |
|---|---|
| Identification code | compound 7 |
| Empirical formula | C18 H20 N2 O2 |
| Formula weight | 296.36 |
| Temperature | 173(2) K |
| Wavelength | 0.71073 Å |
| Crystal system | Monoclinic |
| Space group | C2/c |
| Unit cell dimensions | a = 20.4836(11) Å   α = 90°. |
| | b = 4.6090(2) Å   β = 97.350(2)°. |
| | c = 15.6300(9) Å   γ = 90°. |
| Volume | 1463.49(13) Å$^3$ |
| Z | 4 |
| Density (calculated) | 1.345 Mg/m$^3$ |
| Absorption coefficient | 0.088 mm$^{-1}$ |
| F(000) | 632 |
| Crystal size | 0.30 × 0.25 × 0.20 mm$^3$ |
| Theta range for data collection | 2.00 to 30.55°. |
| Index ranges | −28 <= h <= 28, −6 <= k <= 6, −22 <= l <= 22 |
| Reflections collected | 12938 |
| Independent reflections | 2234 [R(int) = 0.0322] |
| Completeness to theta = 30.55° | 99.6% |
| Absorption correction | Semi-empirical from equivalents |
| Max. and min. transmission | 0.9825 and 0.9739 |
| Refinement method | Full-matrix least-squares on F$^2$ |
| Data/restraints/parameters | 2234/62/129 |
| Goodness-of-fit on F$^2$ | 1.073 |
| Final R indices [I > 2sigma(I)] | R1 = 0.0470, wR2 = 0.1313 |
| R indices (all data) | R1 = 0.0554, wR2 = 0.1442 |
| Largest diff. peak and hole | 0.425 and −0.177 e.Å$^{-3}$ |

(S)-7'-hydroxy-1,1'-dimethyl-1,1',2,2',3,3',4,4'-octahydro-8,8'-biquinolin-7-yl (1R,2S,5R)-2-isopropyl-5-methylcyclohexyl carbonate 8a For a graphical representation of the structure of compound 8a see FIG. 6.

Crystal Data and Structure Refinement for Compound 8a

| | | | |
|---|---|---|---|
| Identification code | compound 8a | | |
| Empirical formula | C31 H42 N2 O4 | | |
| Formula weight | 506.67 | | |
| Temperature | 173(2) K | | |
| Wavelength | 0.71073 Å | | |
| Crystal system | Orthorhombic | | |
| Space group | P2(1)2(1)2(1) | | |
| Unit cell dimensions | a = 12.3403(4) Å | α = 90°. | |
| | b = 14.6166(4) Å | β = 90°. | |
| | c = 15.2085(5) Å | γ = 90°. | |
| Volume | 2743.21(15) Å$^3$ | | |
| Z | 4 | | |
| Density (calculated) | 1.227 Mg/m$^3$ | | |
| Absorption coefficient | 0.080 mm$^{-1}$ | | |
| F(000) | 1096 | | |
| Crystal size | 0.30 × 0.30 × 0.24 mm$^3$ | | |
| Theta range for data collection | 1.93 to 29.25°. | | |
| Index ranges | −16 <= h <= 16, −14 <= k <= 20, −20 <= l <= 19 | | |
| Reflections collected | 33944 | | |
| Independent reflections | 4149 [R(int) = 0.0418] | | |
| Completeness to theta = 29.25° | 100.0% | | |
| Absorption correction | Semi-empirical from equivalents | | |
| Max. and min. transmission | 0.9809 and 0.9763 | | |
| Refinement method | Full-matrix least-squares on F$^2$ | | |
| Data/restraints/parameters | 4149/7/359 | | |
| Goodness-of-fit on F$^2$ | 1.184 | | |
| Final R indices [I > 2sigma(I)] | R1 = 0.0421, wR2 = 0.1068 | | |
| R indices (all data) | R1 = 0.0596, wR2 = 0.1319 | | |
| Absolute structure parameter | −10(10) | | |
| Largest diff. peak and hole | 0.303 and −0.325 e.Å$^{-3}$ | | |

Bifunctional Catalyst 10

For a graphical representation of the structure of compound 10 see FIG. 9.

| | |
|---|---|
| _chemical_formula_moiety | 'C20 H33 N2 O9 P' |
| _chemical_formula_weight | 476.45 |
| _symmetry_cell_setting | Orthorhombic |
| _symmetry_space_group_name_H-M | Pbca loop_ |
| _symmetry_equiv_pos_as_xyz | |
| cell_length_a | 11.7507(3) |
| cell_length_b | 17.9535(4) |
| cell_length_c | 22.0258(5) |
| cell_angle_alpha | 90.00 |
| cell_angle_beta | 90.00 |
| cell_angle_gamma | 90.00 |
| cell_volume | 4646.70(19) |
| cell_formula_units_Z | 8 |
| cell_measurement_temperature | 173(2) |
| cell_measurement_reflns_used | 9390 |
| cell_measurement_theta_min | 2.27 |
| cell_measurement_theta_max | 30.34 |
| exptl_crystal_description | block |
| exptl_crystal_colour | colourless |
| exptl_crystal_size_max | 0.30 |
| exptl_crystal_size_mid | 0.30 |
| exptl_crystal_size_min | 0.25 |
| exptl_crystal_density_meas | ? |
| exptl_crystal_density_diffrn | 1.362 |
| exptl_crystal_density_method | 'not measured' |
| exptl_crystal_F_000 | 2032 |
| exptl_absorpt_coefficient_mu | 0.171 |
| exptl_absorpt_correction_type | multi-scan |
| exptl_absorpt_correction_T_min | 0.9505 |
| exptl_absorpt_correction_T_max | 0.9585 |
| exptl_absorpt_process_details | sadabs |
| diffrn_ambient_temperature | 173(2) |
| diffrn_radiation_wavelength | 0.71073 |
| diffrn_radiation_type | MoK\a |
| diffrn_radiation_source | 'fine-focus sealed tube' |
| diffrn_radiation_monochromator | graphite |
| diffrn_measurement_device_type | 'CCD area detector' |
| diffrn_measurement_method | 'phi and omega scans' |

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An octahydro biquinoline compound of the general formula (V):

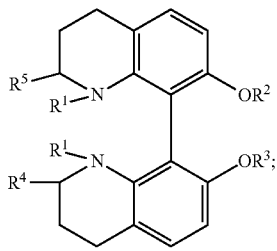

(V)

wherein:
R$^1$ is one of hydrogen, a protective group, and an aliphatic group, wherein the aliphatic group has a main chain of a length of 1 to about 10 carbon atoms, comprising 0 to about 6 heteroatoms selected from the group consisting of N, O, S, Se and Si, R$^2$ and R$^3$ are independent from one another selected from the group consisting of (i) H, (ii) one of an aliphatic, an alicyclic, an aromatic, an arylaliphatic, and an arylalicyclic group with a main chain of a length of 1 to about 30 carbon atoms comprising 0 to about 6 heteroatoms selected from the group consisting of N, O, S, Se and Si, (iii) an ester group —C(O)—R$^{11}$, (iv) a carbonate group —C(O)—O—R$^{11}$, (v) a carbamoyl group —C(O)—N(R$^{11}$)—R$^{12}$ and (vi) a phosphate ester —P(O)(OR$^{11}$)—OR$^{12}$, wherein R$^{11}$ and R$^{12}$ are independent from one another H or one of an aliphatic, a alicyclic, an aromatic, an arylaliphatic, and an arylalicyclic group with a main chain of a length of 1 to about 20 carbon atoms, comprising 0 to about 6 heteroatoms selected from the group consisting of N, O, S, Se and Si, and R$^4$ and R$^5$ are independent from one another H or one of an aliphatic, an alicyclic, an aromatic, an arylaliphatic and an arylalicyclic group with a main chain of a length of 1 to about 30 carbon atoms comprising 0 to about 6 heteroatoms selected from the group consisting of N, O, S, Se and Si.

2. The octahydro biquinoline compound of claim 1, the compound being enriched in one of the enantiomers of general formula (Va) and general formula (Vb);

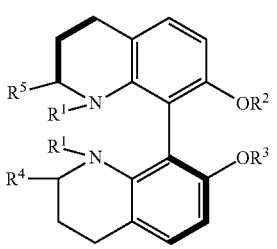

(Va)

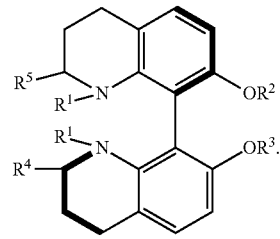

(Vb)

3. The octahydro biquinoline compound of claim 2, being defined by one said enantiomers in an at least essentially pure form.

4. The octahydro biquinoline compound of claim 1, wherein each of R$^1$ is selected from the group consisting of methyl, ethyl, n-propyl, isopropyl, n-butyl, sec-butyl, isobutyl, t-butyl, n-pentyl, isopentyl, sec-pentyl, neo-pentyl and tert-pentyl.

5. The octahydro biquinoline compound of claim 1, wherein the compound is

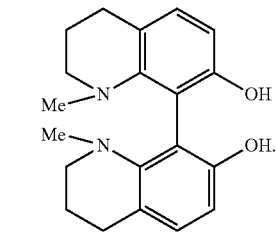 [SMILES: CN1CCCc2ccc(O)c(-c3c(O)ccc4c3N(C)CCC4)c21]

6. A method of forming an octahydro biquinoline compound according to claim 1, the method comprising:
a) providing a biquinolyl compound of general formula (VI):

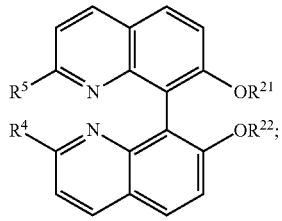

(VI)

wherein:
R$^4$ and R$^5$ are independent from one another H or one of an aliphatic, an alicyclic, an aromatic, an arylaliphatic and an arylalicyclic group with a main chain of a length of 1 to about 30 carbon atoms comprising 0 to about 6 heteroatoms selected from the group consisting of N, O, S, Se and Si, and R$^{21}$ and R$^{22}$ are independent from one another selected from the group consisting of (i) H, (ii) one of an aliphatic, an alicyclic, an aromatic, an arylaliphatic, and an arylalicyclic group comprising 0 to about 6 heteroatoms selected from the group consisting of N, O, S, Se and Si, (iii) an ester group —C(O)—R$^{11}$, (iv) a carbonate group —C(O)—O—R$^{11}$ and (v) a carbamoyl group —C(O)—N(R$^{11}$)—R$^{12}$, wherein R$^{11}$ and R$^{12}$ are independent from one another H or one of an aliphatic, an alicyclic, an aromatic, an arylaliphatic, and an arylalicyclic group with a main chain of a length of 1 to about 20 carbon atoms comprising 0 to about 6 heteroatoms selected from the group consisting of N, O, S, Se and Si, and b) exposing the biquinolyl compound of general formula (VI) to hydrogenation in the presence of a suitable catalyst, thereby allowing the formation of an octahydro biquinoline compound of general formula (XV):

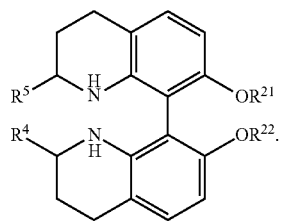

(XV)

7. The method of claim 6, wherein the catalyst is one of Pd/C and Pt/C.

8. The method of claim 6, wherein hydrogenation comprises contacting the biquinolyl compound of general formula (VI) with one of hydrazine, dihydronaphthalene, dihydroanthracene, isopropanol, and formic acid or a salt thereof.

9. The method of claim 6, further comprising contacting the octahydro biquinoline compound of general formula (XV) with a compound of the formula $R^1X$, wherein $R^1$ is an aliphatic group with a main chain of a length of 1 to about 10 carbon atoms, comprising 0 to about 6 heteroatoms selected from the group consisting of N, O, S, Se and Si, and X is one of Chlorine, Bromine, Iodine and —CN, thereby allowing the formation of an octahydro biquinoline compound of general formula (XVI):

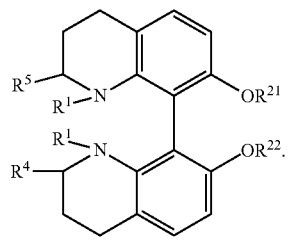

(XVI)

10. The method of claim 6, wherein $R^{21}$ and $R^{22}$ are identical to $R^2$ and $R^3$, respectively, of general Formula (V).

* * * * *